US008672852B2

(12) United States Patent
Gavish

(10) Patent No.: US 8,672,852 B2
(45) Date of Patent: Mar. 18, 2014

(54) APPARATUS AND METHOD FOR BENEFICIAL MODIFICATION OF BIORHYTHMIC ACTIVITY

(75) Inventor: Benjamin Gavish, Mevaseret Zion (IL)

(73) Assignee: Intercure Ltd. (IL)

( * ) Notice: Subject to any disclaimer, the term of this patent is extended or adjusted under 35 U.S.C. 154(b) by 1998 days.

(21) Appl. No.: 10/323,596

(22) Filed: Dec. 13, 2002

(65) Prior Publication Data

US 2004/0116784 A1    Jun. 17, 2004

(51) Int. Cl.
*A61B 5/00* (2006.01)
*A61B 5/02* (2006.01)
*A61B 5/08* (2006.01)
*A61B 5/04* (2006.01)

(52) U.S. Cl.
USPC ............ 600/483; 600/484; 600/500; 600/509; 600/508; 600/309; 600/532; 600/549; 600/546; 600/513; 600/481

(58) Field of Classification Search
USPC ......... 600/483–486, 508–543, 300, 301, 481, 600/490–504, 488, 544, 546, 547, 309, 595
See application file for complete search history.

(56) References Cited

U.S. PATENT DOCUMENTS

| | | | | |
|---|---|---|---|---|
| 3,890,957 A | * | 6/1975 | Freeman | 600/545 |
| 3,942,516 A | * | 3/1976 | Glynn et al. | 600/545 |
| 3,991,304 A | * | 11/1976 | Hillsman | 600/538 |
| 4,031,883 A | * | 6/1977 | Fehmi et al. | 600/545 |
| 4,033,332 A | | 7/1977 | Hardway, Jr. et al. | |
| 4,102,332 A | | 7/1978 | Gressman | |
| 4,195,626 A | | 4/1980 | Schweizer | |
| 4,282,864 A | * | 8/1981 | Pizer | 600/26 |
| 4,312,358 A | | 1/1982 | Barney | |
| 4,355,644 A | * | 10/1982 | Saito | 600/502 |
| 4,381,788 A | | 5/1983 | Douglas | |
| 4,450,843 A | * | 5/1984 | Barney et al. | 600/503 |
| 4,474,185 A | | 10/1984 | Diamond | |
| 4,526,078 A | | 7/1985 | Chadabe | |
| 4,571,680 A | | 2/1986 | Wu | |
| 4,580,574 A | | 4/1986 | Gavish | |

(Continued)

FOREIGN PATENT DOCUMENTS

EP      856334 A2      8/1998
GB      1359005        7/1974

(Continued)

OTHER PUBLICATIONS

B. Gavish, "Repeated Blood Pressure Measurements May Probe Directly an Arterial Property", Abstract, American Journal of Hypertension, May-Jun. 2000, 13(4), Part 2:190A.

(Continued)

*Primary Examiner* — Navin Natnithithadha
(74) *Attorney, Agent, or Firm* — St. Onge Steward Johnston & Reens LLC

(57) ABSTRACT

Apparatus is provided, including a sensor, adapted to generate a sensor signal indicative of biorhythmic activity of a user of the apparatus, the sensor signal having a first characteristic, indicative of a voluntary action of the user, and a second characteristic, indicative of a benefit-related variable of the user. The apparatus also includes a control unit, adapted to receive the sensor signal, and, responsive to the second characteristic, generate an output signal which directs the user to modify a parameter of the voluntary action indicated by the first characteristic.

51 Claims, 5 Drawing Sheets

(56) References Cited

U.S. PATENT DOCUMENTS

| | | | |
|---|---|---|---|
| 4,776,323 A | 10/1988 | Spector | |
| 4,798,538 A | 1/1989 | Yagi | |
| 4,800,893 A * | 1/1989 | Ross et al. | 600/545 |
| 4,827,943 A | 5/1989 | Bornn et al. | |
| 4,883,067 A | 11/1989 | Knispel et al. | |
| 5,050,613 A * | 9/1991 | Newman et al. | 600/483 |
| 5,052,400 A | 10/1991 | Dietz | |
| 5,070,321 A | 12/1991 | Einhorn et al. | |
| 5,076,281 A | 12/1991 | Gavish | |
| 5,137,501 A | 8/1992 | Mertesdorf | |
| 5,143,078 A | 9/1992 | Mather et al. | |
| 5,267,942 A | 12/1993 | Saperston | |
| 5,280,651 A | 1/1994 | Lenihan et al. | |
| 5,329,931 A | 7/1994 | Clauson et al. | |
| 5,343,871 A * | 9/1994 | Bittman et al. | 600/545 |
| 5,367,292 A | 11/1994 | Szoke et al. | |
| 5,423,328 A | 6/1995 | Gavish | |
| 5,434,871 A | 7/1995 | Purdham et al. | |
| 5,465,729 A | 11/1995 | Bittman et al. | |
| 5,485,850 A | 1/1996 | Dietz | |
| 5,533,947 A | 7/1996 | Tomlinson et al. | |
| 5,577,510 A * | 11/1996 | Chittum et al. | 600/522 |
| 5,590,282 A | 12/1996 | Clynes | |
| 5,592,143 A | 1/1997 | Romney et al. | |
| 5,596,994 A | 1/1997 | Bro | |
| 5,621,390 A | 4/1997 | Neal | |
| 5,662,117 A * | 9/1997 | Bittman | 600/545 |
| 5,678,571 A | 10/1997 | Brown | |
| 5,687,291 A | 11/1997 | Smyth | |
| 5,690,691 A | 11/1997 | Chen et al. | |
| 5,730,145 A | 3/1998 | Defares et al. | |
| 5,751,825 A | 5/1998 | Myers | |
| 5,752,509 A | 5/1998 | Lachmann et al. | |
| 5,755,674 A | 5/1998 | Watson | |
| 5,782,878 A | 7/1998 | Morgan | |
| 5,794,615 A | 8/1998 | Estes | |
| 5,800,337 A | 9/1998 | Gavish | |
| 5,827,179 A | 10/1998 | Lichter et al. | |
| 5,830,107 A | 11/1998 | Brigliadoro | |
| 5,899,203 A | 5/1999 | Defares et al. | |
| 5,941,837 A * | 8/1999 | Amano et al. | 600/595 |
| 5,997,482 A | 12/1999 | Vaschillo et al. | |
| 6,001,048 A | 12/1999 | Taylor | |
| 6,001,065 A | 12/1999 | De Vito | |
| 6,013,007 A | 1/2000 | Root et al. | |
| 6,026,335 A * | 2/2000 | Atlas | 700/83 |
| 6,047,203 A | 4/2000 | Sackner et al. | |
| 6,050,940 A | 4/2000 | Braun et al. | |
| 6,076,011 A * | 6/2000 | Hoover | 600/546 |
| 6,081,742 A * | 6/2000 | Amano et al. | 600/513 |
| 6,090,037 A | 7/2000 | Gavish | |
| 6,092,058 A | 7/2000 | Smyth | |
| 6,106,481 A | 8/2000 | Cohen | |
| 6,162,183 A * | 12/2000 | Hoover | 600/534 |
| 6,212,427 B1 * | 4/2001 | Hoover | 600/515 |
| 6,230,047 B1 | 5/2001 | McHugh | |
| 6,241,683 B1 | 6/2001 | Macklem et al. | |
| 6,251,048 B1 | 6/2001 | Kaufman | |
| 6,261,236 B1 * | 7/2001 | Grimblatov | 600/500 |
| 6,305,943 B1 * | 10/2001 | Pougatchev et al. | 434/262 |
| 6,345,202 B2 | 2/2002 | Richmond | |
| 6,436,053 B1 * | 8/2002 | Knapp et al. | 600/538 |
| 6,478,736 B1 | 11/2002 | Mault | |
| 6,519,567 B1 | 2/2003 | Fujii | |
| 6,551,252 B2 * | 4/2003 | Sackner et al. | 600/536 |
| 6,582,342 B2 | 6/2003 | Kaufman | |
| 6,607,484 B2 | 8/2003 | Suzuki | |
| 6,626,843 B2 * | 9/2003 | Hillsman | 600/529 |
| 6,662,032 B1 * | 12/2003 | Gavish et al. | 600/323 |
| 6,672,991 B2 | 1/2004 | O Malley | |
| 6,675,043 B1 | 1/2004 | Prutchi | |
| 6,740,046 B2 * | 5/2004 | Knapp et al. | 600/529 |
| 6,746,247 B2 | 6/2004 | Barton | |
| 6,808,473 B2 | 10/2004 | Hisano et al. | |
| 6,902,513 B1 | 6/2005 | McClure | |
| 7,117,032 B2 * | 10/2006 | Childre et al. | 600/545 |
| 7,207,935 B1 * | 4/2007 | Lipo | 600/28 |
| 7,455,622 B2 | 11/2008 | Watterson et al. | |
| 7,521,623 B2 | 4/2009 | Bowen | |
| 7,544,880 B2 | 6/2009 | Takai et al. | |
| 7,616,097 B1 | 11/2009 | Whang | |
| 7,683,252 B2 | 3/2010 | Oliver et al. | |
| 7,705,230 B2 | 4/2010 | Bowen | |
| 7,728,215 B2 | 6/2010 | Miyajima et al. | |
| 7,737,353 B2 | 6/2010 | Sasaki et al. | |
| 7,738,935 B1 | 6/2010 | Turcott | |
| 7,745,716 B1 | 6/2010 | Murphy | |
| 7,766,794 B2 | 8/2010 | Oliver et al. | |
| 7,771,320 B2 | 8/2010 | Riley et al. | |
| 7,789,800 B1 | 9/2010 | Watterson et al. | |
| 7,805,150 B2 | 9/2010 | Graham et al. | |
| 7,841,967 B1 | 11/2010 | Kahn et al. | |
| 7,867,142 B2 | 1/2011 | Kim et al. | |
| 7,872,188 B2 | 1/2011 | Willis | |
| 7,927,253 B2 | 4/2011 | Vincent et al. | |
| 7,942,824 B1 | 5/2011 | Kayyali et al. | |
| 7,973,231 B2 | 7/2011 | Bowen | |
| 7,985,164 B2 | 7/2011 | Ashby | |
| 8,017,853 B1 | 9/2011 | Rice | |
| 8,029,415 B2 | 10/2011 | Ashby et al. | |
| 8,033,959 B2 | 10/2011 | Oleson et al. | |
| 8,038,576 B2 | 10/2011 | Farinelli et al. | |
| 8,082,920 B2 | 12/2011 | Hughes | |
| 8,101,843 B2 | 1/2012 | Turner | |
| 8,105,208 B2 | 1/2012 | Oleson et al. | |
| 8,162,804 B2 | 4/2012 | Tagliabue | |
| 8,183,453 B2 | 5/2012 | Wagner | |
| 8,200,323 B2 | 6/2012 | DiBenedetto et al. | |
| 8,221,290 B2 | 7/2012 | Vincent et al. | |
| 8,241,184 B2 | 8/2012 | DiBenedetto et al. | |
| 8,251,874 B2 | 8/2012 | Ashby et al. | |
| 8,298,123 B2 | 10/2012 | Hickman | |
| 8,311,654 B2 | 11/2012 | Sako et al. | |
| 2001/0054270 A1 | 12/2001 | Rice | |
| 2002/0040601 A1 | 4/2002 | Fyfe et al. | |
| 2002/0042328 A1 | 4/2002 | Yoo | |
| 2003/0059750 A1 | 3/2003 | Bindler et al. | |
| 2003/0065272 A1 * | 4/2003 | Hillsman | 600/529 |
| 2003/0171189 A1 | 9/2003 | Kaufman | |
| 2004/0015093 A1 * | 1/2004 | Knapp et al. | 600/538 |
| 2004/0077934 A1 | 4/2004 | Massad | |
| 2004/0116784 A1 * | 6/2004 | Gavish | 600/300 |
| 2004/0127335 A1 | 7/2004 | Watterson et al. | |
| 2005/0113703 A1 | 5/2005 | Farringdon et al. | |
| 2005/0126370 A1 | 6/2005 | Takai et al. | |
| 2005/0215397 A1 | 9/2005 | Watterson et al. | |
| 2006/0084551 A1 | 4/2006 | Volpe | |
| 2006/0102171 A1 | 5/2006 | Gavish | |
| 2006/0107822 A1 | 5/2006 | Bowen | |
| 2006/0111621 A1 | 5/2006 | Coppi et al. | |
| 2006/0169125 A1 | 8/2006 | Ashkenazi et al. | |
| 2006/0243120 A1 | 11/2006 | Takai et al. | |
| 2006/0277474 A1 | 12/2006 | Robarts et al. | |
| 2007/0029059 A1 | 2/2007 | Elgarhy et al. | |
| 2007/0033295 A1 | 2/2007 | Marriott | |
| 2007/0044641 A1 | 3/2007 | McKinney et al. | |
| 2007/0060446 A1 | 3/2007 | Asukai et al. | |
| 2007/0074618 A1 | 4/2007 | Vergo | |
| 2007/0113725 A1 | 5/2007 | Oliver et al. | |
| 2007/0113726 A1 | 5/2007 | Oliver et al. | |
| 2007/0118043 A1 | 5/2007 | Oliver et al. | |
| 2007/0135264 A1 | 6/2007 | Rosenberg | |
| 2007/0169614 A1 | 7/2007 | Sasaki et al. | |
| 2007/0203665 A1 | 8/2007 | Darley et al. | |
| 2007/0208531 A1 | 9/2007 | Darley et al. | |
| 2007/0270667 A1 | 11/2007 | Coppi et al. | |
| 2008/0076637 A1 | 3/2008 | Gilley et al. | |
| 2008/0077619 A1 | 3/2008 | Gilley et al. | |
| 2008/0077620 A1 | 3/2008 | Gilley et al. | |
| 2008/0090703 A1 | 4/2008 | Rosenberg | |
| 2008/0096726 A1 | 4/2008 | Riley et al. | |
| 2008/0171943 A1 | 7/2008 | Farringdon et al. | |
| 2008/0183090 A1 | 7/2008 | Farringdon et al. | |
| 2008/0188354 A1 | 8/2008 | Pauws et al. | |

(56) References Cited

U.S. PATENT DOCUMENTS

| | | |
|---|---|---|
| 2008/0214358 A1 | 9/2008 | Ogg et al. |
| 2008/0254946 A1 | 10/2008 | Pauws et al. |
| 2008/0300109 A1 | 12/2008 | Karkanias et al. |
| 2008/0306619 A1 | 12/2008 | Cerra et al. |
| 2009/0024233 A1 | 1/2009 | Shirai et al. |
| 2009/0054741 A1 | 2/2009 | McAleer |
| 2009/0088876 A1 | 4/2009 | Conley et al. |
| 2009/0139389 A1 | 6/2009 | Bowen |
| 2009/0260506 A1 | 10/2009 | Saperston |
| 2009/0270744 A1 | 10/2009 | Prstojevich et al. |
| 2010/0037753 A1 | 2/2010 | Wagner |
| 2010/0186578 A1 | 7/2010 | Bowen |
| 2010/0217099 A1 | 8/2010 | LeBoeuf et al. |
| 2010/0279825 A1 | 11/2010 | Riley et al. |
| 2010/0286532 A1 | 11/2010 | Farringdon et al. |
| 2011/0003665 A1 | 1/2011 | Burton et al. |
| 2011/0016120 A1 | 1/2011 | Haughay et al. |
| 2011/0054290 A1 | 3/2011 | Derchak |
| 2012/0094806 A1 | 4/2012 | Danford |
| 2012/0225412 A1 | 9/2012 | Wagner |

FOREIGN PATENT DOCUMENTS

| | | |
|---|---|---|
| GB | 2035088 A | 6/1980 |
| JP | 04071531 A | 3/1992 |
| JP | 05123300 A | 5/1993 |
| JP | 11042214 A | 2/1999 |
| JP | 2000-051157 A | 2/2000 |
| JP | 2001-518330 | 10/2001 |
| JP | 2002095650 A | 4/2002 |
| WO | WO 97/26822 A2 | 7/1997 |
| WO | WO9814116 A3 | 8/1998 |
| WO | 99/16506 A1 | 4/1999 |
| WO | WO0059580 A1 | 10/2000 |
| WO | WO 01/02049 A2 | 1/2001 |
| WO | WO0102049 A2 | 1/2001 |

OTHER PUBLICATIONS

D.R. Begault, "Challenges Facing 3-D Audio Display Design for Multimedia", Journal of the Acoustical Society of America, 1999, 105(2):1357.

E.M. Wenzel et al., "Localization Using Nonindividualized Head-Related Transfer Functions", Journal of the Acoustical Society of America, Jul. 1993, pp. 111-123.

W.H. Cooke et al., "Controlled Breathing Protocols Probe Human Autonomic Cardiovascular Rhythms", American Journal of Physiology, 1998, 274:H709-H718.

M.V. Pitzalis, et al., "Effect of Respiratory Rate on the Relationship Between RR Interval and Systolic Pressure Fluctuations: A Frequency-Dependent Phenomenon", Cardiovascular Research, 1998, 38:332-339.

L. Bernardi, et al., "Effects of Breating Rate on Oxygen saturation and Exercise Performance in Chronic Heart Failure", The Lancet, May 2, 1998, 351:1308-1311.

A. Mortara et al., "Abnormal Awake Respiratory Patterns are Common in Chronic Heart Failure and May Prevent Evaluation of Autonomic Tone by Measures of Heart Rate Variability", Circulation, Jul. 1997, 96:246-251.

M.T. La Rovere et al., "Baroflex Sensitivity and Heart-Rate Variability in Prediction of Total Cardiac Mortality after Myocardial Infraction", The Lancet, Feb. 14, 1998, 351:478-484.

"Photoplethysmography", 6 pages. 2000. http://www.iboro.ac.uk/departments/el/research/optics/ppgraphy/ppgmain.htm.

M. Busch, "Respiration: What Pilots Need to Know (But Aren't Taught)" AVweb, 1999, 7 pages. http://www.avweb.com/artcles/respirat.html.

P. Gimondo and P. Mirk, "A New Method for Evaluating Small Intestinal Motility Using Duplex Doppler Sonography", AJR American Journal of Roentgenology, Jan. 1997, 168(1):187-192.

A novel by Michael Crichton, "The Andromeda Strain", 1969, pates 100-107.

An office action dated Aug. 25, 2009, which issued during the prosecution of Applicant's Japanese Patent Application No. 2004-561058.

An office action dated May 12, 2009, which issued during the prosecution of Applicant's EP Patent Application No. 03777154.0.

A Supplementary European Search Report dated Nov. 2, 2010, which issued during the prosecution of Applicant's European Patent Application No. EP03784453.

A Translation of an Office Action dated Jan. 26, 2011, which issued during the prosecution of Applicant's Japanese Patent Application No. JP 2007-522123.

An Office Action dated Jun. 24, 2011, which issued during the prosecution of U.S. Appl. No. 12/427,183.

An Office Action dated Sep. 24, 2012, which issued during the prosecution of U.S. Appl. No. 11/958,083.

An Office Action dated Dec. 28, 2012, which issued during the prosecution of U.S. Appl. No. 13/471,582.

\* cited by examiner

APPARATUS AND METHOD FOR BENEFICIAL MODIFICATION OF BIORHYTHMIC ACTIVITY

FIELD OF THE INVENTION

The present invention relates generally to medical devices, and specifically to treatment and diagnostic devices, which provide feedback to a user regarding a physiological variable of the user.

BACKGROUND OF THE INVENTION

Devices which measure a physiological variable of a user and which then provide feedback to the user for the purpose of modifying the variable are well known in the art. U.S. Pat. Nos. 5,076,281, 5,800,337 and 6,090,037 to Gavish, which are incorporated herein by reference, describe methods and devices for modifying biorhythmic activity by measuring one or more variables of a user. The patents describe the generation of a stimulus, which is provided to the user, so as to change the biorhythmic activity of the user in a way that is related in a predetermined way to the monitored biorhythmic activity.

U.S. Pat. No. 5,423,328 to Gavish, which is incorporated herein by reference, describes a stress-detecting device for monitoring respiration, and, in particular, a method for detecting and monitoring circumferential changes in the chest or abdomen of a user resulting from breathing. U.S. Pat. No. 4,580,574 to Gavish, which is incorporated herein by reference, describes a method for non-invasively monitoring properties of living tissue.

U.S. Pat. No. 6,090,037 to Gavish, which is incorporated herein by reference, describes techniques for modification of rhythmic body activity of a user by monitoring biorhythmic activity of the user, and providing the user with a stimulus pattern that resembles but differs from the monitored biorhythmic activity in a way that when followed voluntarily by the user drives a change in the biorhythmic activity.

PCT Patent Publication WO 01/02049 to Gavish et al., which is assigned to the assignee of the present patent application and is incorporated herein by reference, describes techniques for facilitating improving health of a user, including a first sensor, adapted to measure a first physiological variable, which is indicative of a voluntary action of the user, a second sensor, adapted to measure a second physiological variable, which is not entirely under the direct voluntary control of the user, and circuitry, adapted to receive respective first and second sensor signals from the first and second sensors, and responsive thereto, to generate an output signal which directs the user to modify a parameter of the voluntary action. The '049 publication also describes an interventive-diagnostic system comprising a local computing device at a local site, which applies an intervention to a user at the site and receives, from one or more sensors attached to the user, one or more input signals indicative of a physiological condition of the user. One preferred embodiment described includes monitoring breathing movements using one sensor, and guiding the user to modify a breathing pattern in an attempt to optimize blood oxygenation, as measured by a second sensor.

An abstract entitled, "Repeated blood pressure measurements may probe directly an arterial property," *American Journal of Hypertension* (April, 2000); 13(4), part 2: 190A, by B. Gavish, which is incorporated herein by reference, proposes that the slope of a line relating multiple systolic and diastolic blood pressure measurements is a physiologically-meaningful parameter.

An article entitled, "Challenges facing 3-D audio display design for multimedia," *Journal of the Acoustical Society of America* (1999); J 105:1357, by D. R. Begault, which is incorporated herein by reference, describes the production and psychophysiological implications of 3-D sound, which enables listeners to perceive the direction of a sound source in three dimensions. Another article, entitled, "Localization using nonindividualized head-related transfer functions," by Wenzel et al., *Journal of the Acoustical Society of America* (July, 1993); 94(1), pp. 222-234, which is incorporated herein by reference, describes the synthesis of 3-D sound, so as to enable listeners to perceive the 3-D direction and localization of a virtual sound source. In addition, a cassette distributed by NASA/Ames Research Center, entitled, "Demonstration of 3-D auditory display," allows a listener using a normal cassette player and standard earphones to experience the three-dimensional effect.

Other articles of interest, all of which are incorporated herein by reference, include:

(a) an article by Cooke et al., entitled, "Controlled breathing protocols probe human autonomic cardiovascular rhythms," *American Journal of Physiology*, (1998); 274: H709-H718

(b) an article by Pitzalis et al., entitled, "Effect of respiratory rate on the relationship between RR interval and systolic blood pressure fluctuations: a frequency-dependent phenomenon," *Cardiovascular Research* (1998); 38:332-339

(c) an article by Bernardi et al., entitled, "Effect of breathing rate on oxygen saturation and exercise performance in chronic heart failure," *The Lancet* (May 2, 1998); 351:1308-1311

(d) an article by Mortara et al., entitled, "Abnormal awake respiratory patterns are common in chronic heart failure and may prevent evaluation of autonomic tone by measures of heart rate variability," *Circulation* (Jul. 1, 1997); 96:246-252

(e) an article by La Rovere et al., entitled, "Baroreflex sensitivity and heart-rate variability in prediction of total cardiac mortality after myocardial infarction," *The Lancet* (Feb. 14, 1998); 351:478-484

(f) an article by Gimondo and Mirk, entitled, "A new method for evaluating small intestinal motility using duplex Doppler sonography," *AJR American Journal of Roentgenology* (January, 1997); 168(1):187-192.

Devices which are at least partially operated remotely are also known in the art. U.S. Pat. No. 4,102,332 to Gessman, which is incorporated herein by reference, describes a device for remote telephonic resuscitation. The device includes an electrocardiograph and a defibrillator which are carried by a user with a known history of cardiac symptoms, and which may be used to diagnose and treat acute cardiac symptoms. In order to facilitate the diagnosis and treatment, the device may be connected to a telephone line, so that a remote physician may make the diagnosis and perform the treatment.

U.S. Pat. No. 4,195,626 to Schweizer, which is incorporated herein by reference, describes a biofeedback chamber for applying audible, visual electrical or tactile stimuli to a subject according to a rhythmic pattern. The subject's reactions are measured, analyzed and used to control the stimuli.

U.S. Pat. No. 5,782,878 to Morgan, which is incorporated herein by reference, describes a system including an external defibrillator, a defibrillator communicator, and a communication network. In order to perform a defibrillation, information is transmitted back and forth between a patient and a communication station.

U.S. Pat. No. 5,794,615 to Estes, which is incorporated herein by reference, describes a system for treatment of congestive heart failure. The patent describes controlling the flow rate of a pressurized gas delivered to a patient during the two phases of the respiratory cycle independently. The system may be fully automated responsive to feedback provided by a flow sensor that determines the estimated patient flow rate.

U.S. Pat. No. 5,678,571 to Brown, which is incorporated herein by reference, describes a method for treating a medical condition in a patient comprising choosing a psychological strategy for treating the medical condition, and then encoding electronic instructions for an interactive video game. The game implements the psychological strategy, and loads the electronic instructions into a microprocessor-based unit equipped with a display for displaying the video game. The game contains scoring instructions to quantitatively analyze the medical condition of the patient, counseling instructions and self-care instructions. The video game can be used in conjunction with a physiological variable measuring device connected to the microprocessor-based unit.

U.S. Pat. No. 5,596,994 to Bro, which is incorporated herein by reference, describes an automated and interactive positive motivation system that allows a physician, counselor or trainer to produce and send a series of motivational messages and/or questions to a client to change or reinforce a specific behavioral problem.

U.S. Pat. No. 5,752,509 to Lachmann et al., which is incorporated herein by reference, describes a system for artificially ventilating a patient. The ventilation system has a gas delivery unit for delivering controllable inspiration pulses to a patient, a monitoring unit for measuring at least one parameter related to the function of the circulatory system, such as a blood gas analyzer, and a control unit for determining an optimal peak inspiratory pressure and pressure amplitude for the inspiration pulse, based on the measured circulatory system parameter.

Descriptions of respiratory monitoring apparatus which assess capacitance are found in U.S. Pat. Nos. 5,485,850 to Dietz, 4,033,332 to Hardway et al., 4,381,788 to Douglas, 4,474,185 to Diamond, and in U.S. Pat. Nos. 5,367,292, 5,070,321, and 5,052,400, all of which are incorporated herein by reference.

U.S. Pat. No. 5,690,691 to Chen et al., which is incorporated herein by reference, describes a portable or implantable gastric pacemaker, which includes multiple electrodes that are positioned on an organ in the gastrointestinal (GI) tract, so as to deliver electrical stimulation to pace the peristaltic movement of material through the GI tract.

U.S. Pat. Nos. 5,590,282 and 4,526,078, which are incorporated herein by reference, describe techniques for causing a computer to compose music.

U.S. Pat. No. 4,883,067 to Knispel et al., which is incorporated herein by reference, describes a method for translating a subject's electroencephalogram into music, so as to induce and control various psychological and physiological states of the subject.

U.S. Pat. No. 4,798,538 to Yagi, which is incorporated herein by reference, describes an abdominal respiration training system. The state of the abdominal respiration of a person is measured by a sensor attached to the abdominal region, and the detected breath pattern is compared with an ideal breath pattern.

U.S. Pat. No. 5,827,179 to Lichter et al., which is incorporated herein by reference, describes a real-time biological data processing PC card, adapted to input and process biological data from one or more biological data sensors, and to be interchangeable with other real-time biological data processing PC cards.

U.S. Pat. No. 6,050,940 to Braun et al., which is incorporated herein by reference, describes a general-purpose, low-cost system that provides comprehensive physiological data collection, with extensive data object oriented programmability and configurability for a variety of medical as well as other analog data collection applications.

U.S. Pat. No. 6,001,065 to DeVito, which is incorporated herein by reference, describes techniques for measuring and performing real-time FFT analysis of bioelectrical signals such as electroencephalogram (EEG) and electromyography (EMG) signals for the control of systems. Passive and active interaction with various electronic media such as video games, movies, music, virtual reality, and computer animations is also described.

In a number of cardiovascular diseases, including CHF, and pulmonary diseases, including COPD, breathing patterns display irregularities. These irregularities are known markers for disease-related mortality and morbidity. Typical irregularities include Cheyne-Stokes breathing (recurrent episodes of central apnea alternating with hyperpnea), amplitude-modulated breathing (periodic breathing) at a rate of about one modulation per minute, repeated sighs, and breathing at random amplitudes and periods. A reduction in breathing pattern irregularity indicates an improvement in health. The impairment of cardiovascular reflexes, which control blood pressure and volume in attempt to minimize fluctuations in blood supply to organs (homeostasis), is also clinically significant in cardiovascular and psychosomatic diseases.

SUMMARY OF THE INVENTION

In some embodiments of the present invention, a device for beneficial modification of biorhythmic activity comprises a control unit and at least one physiological sensor, adapted to be applied to a user and to generate a sensor signal indicative of biorhythmic activity of the user. The control unit is adapted to receive and analyze the sensor signal, and, responsive to the analysis, perform an intervention on the user, typically by generating an output signal. The analysis typically includes identifying in the sensor signal a first and a second characteristic. The first characteristic is indicative of a voluntary action of the user, typically one aspect of the user's biorhythmic activity. The second characteristic is indicative of a physiological variable of the user that is desired to be improved and over which most persons do not usually exert voluntary control (a "benefit-related variable," as used in the context of the present patent application and in the claims). The output signal directs the user to modify a parameter of the voluntary action, so as to cause an improvement in the benefit-related variable.

During a typical session of use, the device continuously senses biorhythmic activity, identifies the first and second characteristics, and modifies the intervention responsive to analysis of the characteristics. The user typically uses the device during multiple sessions that extend over a period of time, generally days, months or years. Each session typically has a length of between about 10 and about 20 minutes, most typically about 15 minutes.

In some embodiments of the present invention, the voluntary action of the user comprises respiration, and the modifiable parameters of the voluntary action include one or more timing parameters of the respiration. The output signal typically comprises an intelligible stimulus, such as a sound pattern and/or dynamic graphical pattern, which is generated by the device responsive to the analysis according to one or more predefined criteria. The stimulus is typically intended to modify respiration of the user, for example, by training the user to initiate a new breathing pattern. For example, the output signal may direct the user to change the timing of inspiration and expiration so as to cause a reduction in a ratio of inspiration to expiration. For some interventions, it is desirable to reduce this ratio, for example typically towards 1:4, from a pre-intervention level typically of 1:1 or 1:2. For some applications, the benefit-related variable is an amplitude (or frequency) of the respiration.

Routine use of the device may increase the degree of voluntary control a user has over a disease-related breathing irregularity, such as those described in the Background of the Invention. Such routine use may thus be beneficial for reducing mortality and morbidity related to some medical conditions. For example, the use of the device may be beneficial for treating the following conditions:

some cardiovascular diseases, including congestive heart failure (CHF);
some pulmonary diseases, including chronic obstructive pulmonary disease (COPD);
some neurological diseases, such as panic disorder;
hypertension; and
hyperactivity, such as in children.

In some embodiments of the present invention, the device comprises a first and a second sensor, which generate a first sensor signal and a second sensor signal, respectively. The first characteristic is derived from the first and/or the second sensor signal, while the second characteristic is derived from both the first and the second sensor signals. For some applications, the first and second sensors comprise respective respiration sensors that monitor abdominal breathing and thoracic breathing, respectively. In these applications, the voluntary action of the user comprises respiration, and the modifiable parameters of the voluntary action typically include one or more timing parameters of the respiration. The benefit-related variable is (a) a phase difference between abdominal breathing and thoracic breathing, which the intervention attempts to change; (b) a ratio of abdominal breathing amplitude to thoracic breathing amplitude, which the intervention attempts to increase; or (c) a combination of (a) and (b). For example, in CHF and COPD the abdominal muscles often exhibit reduced functionality, as indicated by a reduced ratio of abdominal to thoracic breathing amplitude. The intervention attempts to increase this ratio and thereby have a positive effect on aspects of these conditions.

In some embodiments of the present invention, the device comprises a plurality of sensors adapted to measure cardiovascular reflexes. The sensors generate a plurality of sensor signals, from which both the first and second characteristics are derived. For example, baroreflex sensitivity can be monitored non-invasively by detecting respiratory modulation of the heart rate and/or skin blood volume changes, measured using plethysmography. In these applications, the voluntary action of the user comprises respiration, and the modifiable parameters of the voluntary action typically include one or more timing parameters of the respiration. The benefit-related variable is typically a measure of baroreflex sensitivity, which is typically expressed as a cross-correlation between two aspects of one of the sensor signals, such as time periods and signal amplitudes.

In some embodiments of the present invention, the first and second characteristics are monitored simultaneously. In other embodiments, the first and second characteristics are monitored non-simultaneously. For example, during a first phase of operation, the device may record a baseline measurement of values of the second characteristic, which measurement is a diagnostic indication of the physiological status of the user before undergoing the device-generated intervention. During a second phase of operation, the device performs the intervention responsive to this baseline measurement.

In some embodiments of the present invention, the device comprises a first and a second sensor. The first sensor generates a first sensor signal indicative of a biorhythmic activity, from which the first characteristic is derived, and the second sensor generates a second sensor signal, from which the second characteristic is derived.

Typically, the device stores the sensor signals and analyzed characteristics generated over time ("stored data") in a data logger, which typically comprises an electronic memory and/or a permanent storage medium. The optional use of an interchangeable data logger, such as a "smart card," enables multiple users to use the device, each retaining his or her own stored data.

For some applications, the device is configured to operate in a diagnostic mode, in which the device does not perform an intervention. In this mode, the device stores the stored data in the data logger, for later analysis.

The data logger typically retains stored data from multiple sessions of use of the device. Stored data may include trends calculated from previous sessions, and can be displayed alpha-numerically or graphically by the device pursuant to operator instructions. The stored data may enable evaluation of the success of a routine or repeated use of the device. Additionally, some aspects of the stored data (including current and past use of the device) can be displayed so as to provide help and feedback to the user. For example, the displayed data may motivate the user to make the desired modifications to biorhythmic activity, during an intervention or when the user is not currently using the device.

In some embodiments of the present invention, one or more health status parameters are derived from a third characteristic identified in the sensor signal, or received from a separate health status sensor. These parameters are associated with physiological variables which it is desired to keep in prescribed limits to avoid undesired effects. Examples of such parameters include respiration rate, which should be monitored to avoid hyperventilation; heart rate, which should be monitored to prevent the use of the system when even a minimal effort may cause tachycardia in patients with severe heart failure; weight; height; age; ECG; and blood pressure. For example, during interventions to reduce the inspiration-to-expiration ratio, a health status parameter, such as amplitude of respiration, is interpreted as an indicator of the benefit of the intervention. If the parameter exceeds or passes a certain threshold value (e.g., an amplitude of respiration greater than about three times resting respiration amplitude), subsequent changes in the output signal which engender changes in the inspiration-to-expiration ratio are delayed until the parameter again falls below the threshold value.

Techniques described herein may be used in conjunction with techniques described in U.S. patent application Ser. No. 09/611,304, filed Jul. 6, 2000, entitled, "Interventive-diagnostic device," and in PCT Patent Publication WO 01/02049 to Gavish et al., which are assigned to the assignee of the present patent application and are incorporated herein by reference, including the remotely-mediated techniques described therein. For example, pursuant to operator instructions, stored data may be downloaded to a local or remote site for further processing, and/or used for generating a report to be used by a healthcare provider for checking compliance, performance and/or outcomes of routine use of the device.

For some applications, some of the online or offline feedback to the user is delivered by voice or audiovisual messages. Such feedback may include, for example, errors in use and suggested corrective action, guidance synchronized with the intervention when needed, warning messages, and/or a summary of compliance and/or performance data.

A "diagnosis" is to be understood in the disclosure and in the claims as the generation of an evaluation responsive to one or more physiological variables of the user. The evaluation may be generated before, during, and/or after the intervention is performed. For example, long-term variations in a user's breathing pattern regularity may be determined by comparing a pre-intervention evaluation with during- and/or post-treatment evaluations. Alternatively or additionally, evaluations generated during intervention may be used to monitor the current status of a user's reflex system. Further alternatively or additionally, relief from measurable symptoms is typically measured by comparing pre- and post-intervention evaluations. For some applications, the device records a post-treatment measurement of the second characteristic (e.g., changes in breathing regularity after exercise compared with before exercise), in order to enable measurement of the acute benefit of the treatment. This, for example, is used to indicate the success of the treatment in relieving dyspnea (breathlessness), which is a beneficial therapeutic action in the treatment of CHF and COPD.

A "user" is to be understood in the disclosure and in the claims as the person whose biorhythmic activity is monitored, while an "operator" may be the user or a person other than the user, e.g., a healthcare worker, who, for example, configures the device and/or manages the stored data either at a remote facility or offline through the device interface, in order to generate diagnoses or reports, or to guide the user in the use of the device.

There is therefore provided, in accordance with an embodiment of the present invention, apparatus including:
  a sensor, adapted to generate a sensor signal indicative of biorhythmic activity of a user of the apparatus, the sensor signal having a first characteristic, indicative of a voluntary action of the user, and a second characteristic, indicative of a benefit-related variable of the user; and
  a control unit, adapted to receive the sensor signal, and, responsive to the second characteristic, generate an output signal which directs the user to modify a parameter of the voluntary action indicated by the first characteristic.

In an embodiment, the control unit is adapted to identify the first and the second characteristics in the sensor signal. In an embodiment, the control unit is adapted to generate the output signal responsive to the first characteristic and the second characteristic.

In an embodiment, the control unit is adapted to:
  identify an aspect of the first characteristic indicative of the user having modified the parameter to a desired extent, and
  responsive to identifying the aspect of the first sensor signal, generate a new output signal, to direct the user to further modify the parameter of the voluntary action.

The first characteristic may be selected from the list consisting of: a period of an aspect of the sensor signal, a rate of an aspect of the sensor signal, a rise time of an aspect of the sensor signal, a fall time of an aspect of the sensor signal, a time derivative at a point of an aspect of the sensor signal, a maximum of the time derivative, a minimum of the time derivative, an amplitude of a maximum of an aspect of the sensor signal averaged over two or more biorhythmic cycles of the aspect, and an amplitude of a minimum of an aspect of the sensor signal averaged over two or more cycles of the aspect, and the sensor is adapted to generate the sensor signal having the first characteristic. Alternatively or additionally, the first characteristic includes a time difference between two points of an aspect of the sensor signal, the points characterizing a single cycle of the biorhythmic activity. Further alternatively or additionally, the first characteristic includes a signal value difference between two points of an aspect of the sensor signal, the points characterizing a single cycle of the biorhythmic activity.

The second characteristic may include a variability of an aspect of the biorhythmic activity, the aspect selected from the list consisting of: an envelope of the biorhythmic activity, an amplitude of the biorhythmic activity, a period of the biorhythmic activity, a standard deviation (SD) of the envelope, an SD of the amplitude, and an SD of the period, in which case the control unit is adapted to generate the output signal responsive to the variability of the aspect.

In an embodiment, the apparatus includes a health status sensor, adapted to generate a health status signal indicative of a health status parameter of the user, which health status parameter is indicative of a state of health of the user, and the control unit is adapted to receive the health status signal, and to determine whether the health status parameter passes a threshold value.

In an embodiment, the control unit includes a memory, and the control unit is adapted to:
  store, in the memory, values of the second characteristic generated over a first period of time, during which first period the control unit withholds generating the output signal, and
  during a second period of time after the conclusion of the first period, generate the output signal responsive to the stored values of the second characteristic.

In an embodiment, the control unit is adapted to generate the output signal in the form of a game, and to alter parameters of the game so as to induce the user to modify the parameter of the voluntary action.

For some applications, the biorhythmic activity includes muscle activity of the user, and the sensor is adapted to generate the sensor signal indicative of the muscle activity. Alternatively or additionally, the biorhythmic activity includes cardiac activity, and the sensor is adapted to generate the sensor signal indicative of the cardiac activity.

In an embodiment, the sensor is adapted to be coupled to a belt, which belt is adapted to be placed around a torso of the user.

The sensor may be selected from the list consisting of: a fast-responding temperature sensor, an electrocardiogram (ECG) monitor, at least one electromyography (EMG) electrode, an electroencephalogram (EEG) monitor, a blood gas concentration sensor, a photoelectric sensor, a photoplethysmographic sensor, a pulse oximeter, and a laser Doppler sensor.

The sensor may also be adapted to sense a concentration of a gas emitted from a tissue of the user, or a microvascular property of the user. In an embodiment, the sensor includes an electrical impedance sensor, adapted to sense an electrical impedance of at least one organ of the user.

In an embodiment, the control unit is adapted to configure the output signal to direct the user to modify the parameter of the voluntary action so as to cause an improvement in the benefit-related variable. For some applications, the benefit-related variable is an amplitude of respiration of the user, and the control unit is adapted to configure the output signal to direct the user to modify the parameter of the voluntary action so as to cause the improvement in the amplitude of the respiration. Alternatively, the benefit-related variable is a measure of baroreflex sensitivity of the user, and the control unit is adapted to configure the output signal to direct the user to modify the parameter of the voluntary action so as to cause the improvement in the measure of baroreflex sensitivity.

In an embodiment, the benefit-related variable is selected from the list consisting of: a frequency of respiration of the user, a blood pressure of the user, a blood oxygenation saturation of the user, an end-tidal CO2 level of the user, a tissue oxygenation level of the user, a pulse-wave velocity of the user, variations in a skin blood volume of the user, a measure of peak air flow of the user, an amplitude of a skin pulse volume of the user, an arterial compliance of the user, and a parameter of an electrocardiogram of the user, and the control unit is adapted to configure the output signal to direct the user to modify the parameter of the voluntary action so as to cause the improvement in the benefit-related variable.

In an embodiment, the control unit is adapted to configure the output signal to direct the user to modify the parameter of the voluntary action so as to cause the improvement in the benefit-related variable, so as to treat a cardiovascular disease of the user.

In an embodiment, the control unit is adapted to configure the output signal to direct the user to modify the parameter of the voluntary action so as to cause the improvement in the benefit-related variable, so as to treat a pulmonary disease of the user.

In an embodiment, the control unit is adapted to configure the output signal to direct the user to modify the parameter of the voluntary action so as to cause the improvement in the benefit-related variable, so as to treat a condition of the user selected from the list consisting of: a neurological disease, hypertension, and hyperactivity.

In an embodiment, the output signal includes an intelligible stimulus, and the control unit is adapted to generate the intelligible stimulus, so as to direct the user to modify the parameter of the voluntary action. The intelligible stimulus may include at least one stimulus selected from the list consisting of: an image, alpha-numeric text, a sound, a sound pattern, and a dynamic graphical pattern, and the control unit is adapted to generate the stimulus, so as to direct the user to modify the parameter of the voluntary action. In an embodiment, the apparatus includes a speaker, and the intelligible stimulus includes music, and the control unit is adapted to drive the speaker to generate the music, so as to direct the user to modify the parameter of the voluntary action.

In an embodiment, the sensor is adapted to generate the sensor signal having a third characteristic indicative of a health status parameter of the user, which health status parameter is indicative of a state of health of the user, and the control unit is adapted to determine whether the health status parameter passes a threshold value. For some applications, the control unit is adapted to withhold generating the output signal responsive to determining that the third characteristic passes the threshold value. Alternatively or additionally, the control unit is adapted to generate an alarm signal responsive to determining that the third characteristic passes the threshold value.

In an embodiment, the biorhythmic activity includes respiration, and the sensor is adapted to generate the sensor signal indicative of the respiration. The sensor may be selected from the list consisting of: a flow meter, adapted to sense respiration by sensing respiratory air flow of the user; a microphone, adapted to sense respiration by sensing breath sounds of the user; and a heated wire, adapted to sense respiration by sensing respiratory air flow of the user.

In an embodiment, the voluntary action includes the respiration, and the control unit is adapted to generate the output signal to direct the user to modify a parameter of the respiration. In an embodiment, the first characteristic includes at least one breathing parameter selected from: inspiration time and expiration time, and the sensor is adapted to generate the sensor signal having the first characteristic. Alternatively or additionally, the first characteristic includes an average frequency of a skin pulse volume of the user, and the sensor is adapted to generate the sensor signal having the first characteristic. Further alternatively or additionally, the first characteristic includes an end-tidal CO2 level of the user, and the sensor is adapted to generate the sensor signal having the first characteristic.

In an embodiment, the parameter of the respiration includes one or more timing parameters of the respiration, and the control unit is adapted to generate the output signal to direct the user to modify the timing parameters of the respiration. The timing parameters may include a pattern of inspiration and expiration of the user, in which case the control unit is adapted to generate the output signal to direct the user to modify the pattern. In an embodiment, the control unit is adapted to generate the output signal to direct the user to modify the pattern so as to reduce a ratio of a time period of the inspiration to a time period of the expiration.

In an embodiment, the sensor is adapted to sense a change in a property of an organ of the user, the property selected from the list consisting of: a circumference of the organ, a volume of the organ, and a pressure of the organ. The sensor may be selected from the list consisting of: a finger plethysmograph, a pressure cuff, and a strain gauge.

In an embodiment, the first characteristic includes a plurality of first characteristics indicative of the voluntary action of the user, and the control unit is adapted to generate the output signal responsive to at least one relationship among the plurality of first characteristics. In an embodiment, the control unit is adapted to determine the relationship using an analysis technique selected from: cross-correlation analysis in a frequency domain and cross-correlation analysis in a time domain.

In an embodiment, the first characteristic includes a relationship among two or more spectral components that are defined by points in the sensor signal.

In an embodiment, the first characteristic includes at least one spectral component that is defined by points in the sensor signal. The spectral component may be defined by a first subset of points in the sensor signal, the first subset of points being located among a second subset of points in the sensor signal different from the first subset of points, the first subset of points sharing a common property. The common property may be selected from the list consisting of: local maxima and local minima of the sensor signal.

There is also provided, in accordance with an embodiment of the present invention, apparatus including:

a first sensor, adapted to measure a voluntary physiological variable, which is indicative of a voluntary action of a user of the apparatus, and to generate a voluntary sensor signal responsive thereto;

a second sensor, adapted to measure a benefit-related physiological variable, indicative of an amplitude of respiration of the user, and to generate a benefit-related sensor signal responsive thereto; and a control unit, adapted to receive the voluntary and benefit-related sensor signals, and, responsive thereto, to generate an output signal which directs the user to modify a parameter of the voluntary action.

In an embodiment, the voluntary action includes respiration of the user, and the control unit is adapted to generate the output signal to direct the user to modify a parameter of the respiration.

In an embodiment, the control unit is adapted to configure the output signal to direct the user to modify the parameter of the voluntary action so as to cause an improvement in the benefit-related physiological variable.

There is further provided, in accordance with an embodiment of the present invention, apparatus including:
- a first sensor, adapted to generate a first sensor signal;
- a second sensor, adapted to generate a second sensor signal; and
- a control unit, adapted to:
- receive the first and second sensor signals,
- identify a first characteristic in at least one of the first sensor signal and the second sensor signal, the first characteristic indicative of a voluntary action of a user of the apparatus;
- derive a second characteristic from the first and second sensor signals in combination, and
- responsive to the second characteristic, generate an output signal which directs the user to modify a parameter of the voluntary action.

In an embodiment, the control unit is adapted to configure the output signal to direct the user to modify the parameter of the voluntary action so as to cause an improvement in a physiological variable of the user of which the second characteristic is indicative.

In an embodiment, the control unit is adapted to generate the output signal responsive to the first characteristic and the second characteristic.

There is still further provided, in accordance with an embodiment of the present invention, apparatus including:
- a first sensor, adapted to measure abdominal breathing of a user of the apparatus, and to generate an abdominal breathing sensor signal;
- a second sensor, adapted to measure thoracic breathing of the user, and to generate a thoracic breathing sensor signal; and
- a control unit, adapted to receive the abdominal and thoracic breathing sensor signals, and, responsive thereto, to generate an output signal which directs the user to modify a parameter of respiration of the user.

In an embodiment, the parameter of the respiration includes a timing parameter of the respiration, and the control unit is adapted to generate the output so as to direct the user to modify the timing parameter of the respiration.

In an embodiment, the control unit is adapted to configure the output signal to direct the user to modify the parameter of the respiration so as to cause an improvement in a physiological variable of the user of which the abdominal and thoracic breathing sensor signals are indicative. The physiological variable may include a phase difference between the abdominal breathing and the thoracic breathing, in which case the control unit is adapted to configure the output signal to direct the user to modify the parameter of the respiration so as to cause a change in the phase difference. The physiological variable may include a ratio of abdominal breathing amplitude to thoracic breathing amplitude, in which case the control unit is adapted to configure the output signal to direct the user to modify the parameter of the respiration so as to cause an increase in the ratio.

In an embodiment, the control unit is adapted to configure the output signal to treat a condition of the user selected from the list consisting of: congestive heart failure and chronic obstructive pulmonary disease.

There is additionally provided, in accordance with an embodiment of the present invention, apparatus including:
- a sensor, adapted to generate a sensor signal indicative of respiration of a subject whose autonomic control of breathing is impaired; and
- a control unit, adapted to receive the sensor signal, and, responsive thereto, to generate an output signal which causes the subject to involuntarily modify a parameter of the respiration.

In an embodiment, the control unit is adapted to generate the output signal slightly out of phase with the respiration.

In an embodiment, the sensor is adapted to be applied to the subject when the subject is sleeping. In an embodiment, the control unit is adapted to generate the output signal so as to treat sleep apnea of the subject.

In an embodiment, the sensor is adapted to be applied to the subject when the subject is unconscious. In an embodiment, the sensor is adapted to be applied to the subject when the subject is in a coma or is anesthetized.

There is yet additionally provided, in accordance with an embodiment of the present invention, diagnostic apparatus, including:
- a sensor, adapted to measure a voluntary physiological variable, which is indicative of a voluntary biorhythmic action of a user of the apparatus, and to generate a sensor signal responsive thereto; and
- a control unit, adapted to receive the sensor signal, to determine a level of a variation over time of the voluntary action, and, responsive thereto, to generate an output signal.

In an embodiment, the control unit is adapted to determine the level of the variation so as to facilitate a diagnosis.

In an embodiment, the sensor includes a respiration sensor.

In an embodiment, the control unit is adapted to determine a level of variation over time of an envelope of the signal. Alternatively or additionally, the control unit is adapted to determine a level of variation over time of an amplitude of the signal. Further alternatively or additionally, the control unit is adapted to determine a level of variation over time of at least one of: a period of the signal and a rate of the signal.

There is also provided, in accordance with an embodiment of the present invention, diagnostic apparatus, including:
- a plethysmography sensor, adapted to generate a sensor signal; and
- a control unit, adapted to receive the sensor signal, to determine a level of a variation over time of the signal, and, responsive thereto, to generate an output signal.

In an embodiment, the control unit is adapted to determine the level of variation so as to facilitate a diagnosis. Alternatively or additionally, the control unit is adapted to determine a level of variation over time of an envelope of the signal. Further alternatively or additionally, the control unit is adapted to determine a level of variation over time of an amplitude of the signal. Still further alternatively or additionally, the control unit is adapted to determine a level of variation over time of at least one of: a period of the signal and a rate of the signal.

There is further provided, in accordance with an embodiment of the present invention, a method for facilitating improving health of a user, including:
- receiving a sensor signal indicative of biorhythmic activity of the user, the sensor signal having a first characteristic, indicative of a voluntary action of the user, and a second characteristic, indicative of a benefit-related variable of the user; and responsive to the second characteristic, generating an output signal which directs the user to modify a parameter of the voluntary action indicated by the first characteristic.

In an embodiment, receiving the sensor signal includes monitoring breathing movements of the user via changes in a circumference of a portion of a torso of the user.

There is still further provided, in accordance with an embodiment of the present invention, a method for facilitating improving health of a user, including:

receiving a voluntary sensor signal indicative of a voluntary physiological variable, which voluntary physiological variable is indicative of a voluntary action of the user;

receiving a benefit-related sensor signal indicative of a benefit-related physiological variable, which benefit-related physiological variable is indicative of an amplitude of respiration of the user; and responsive to the voluntary sensor signal and the benefit-related sensor signal, generating an output signal which directs the user to modify a parameter of the voluntary action.

There is additionally provided, in accordance with an embodiment of the present invention, a method for facilitating improving health of a user, including:

receiving a first sensor signal and a second sensor signal;

identifying a first characteristic in at least one of the first sensor signal and the second sensor signal, the first characteristic indicative of a voluntary action of the user;

deriving a second characteristic from the first and second sensor signals in combination; and responsive to the second characteristic, generating an output signal which directs the user to modify a parameter of the voluntary action.

There is yet additionally provided, in accordance with an embodiment of the present invention, a method for facilitating improving health of a user, including:

receiving an abdominal breathing sensor signal indicative of abdominal breathing of the user;

receiving a thoracic breathing sensor signal indicative of thoracic breathing of the user;

responsive to the abdominal and thoracic breathing sensor signals, generating an output signal which directs the user to modify a parameter of respiration of the user.

There is also provided, in accordance with an embodiment of the present invention, a method including:

receiving a sensor signal indicative of respiration of a subject whose autonomic control of breathing is impaired; and responsive to the sensor signal, generating an output signal which causes the subject to involuntarily modify a parameter of the respiration.

There is further provided, in accordance with an embodiment of the present invention, a method for facilitating a diagnosis of a user, including:

measuring a voluntary physiological variable, which is indicative of a voluntary biorhythmic action of the user, and generating a sensor signal responsive thereto;

receiving the sensor signal;

determining a level of a variation over time of the voluntary action; and responsive to the level of the variation, generating an output signal.

There is still further provided, in accordance with an embodiment of the present invention, a method for facilitating a diagnosis of a user, including:

generating a sensor signal using plethysmography;

receiving the sensor signal;

determining a level of a variation over time of the signal; and responsive to the level of the variation, generating an output signal.

The present invention will be more fully understood from the following detailed description of embodiments thereof, taken together with the drawings, in which:

DETAILED DESCRIPTION OF EMBODIMENTS

Figure 1:
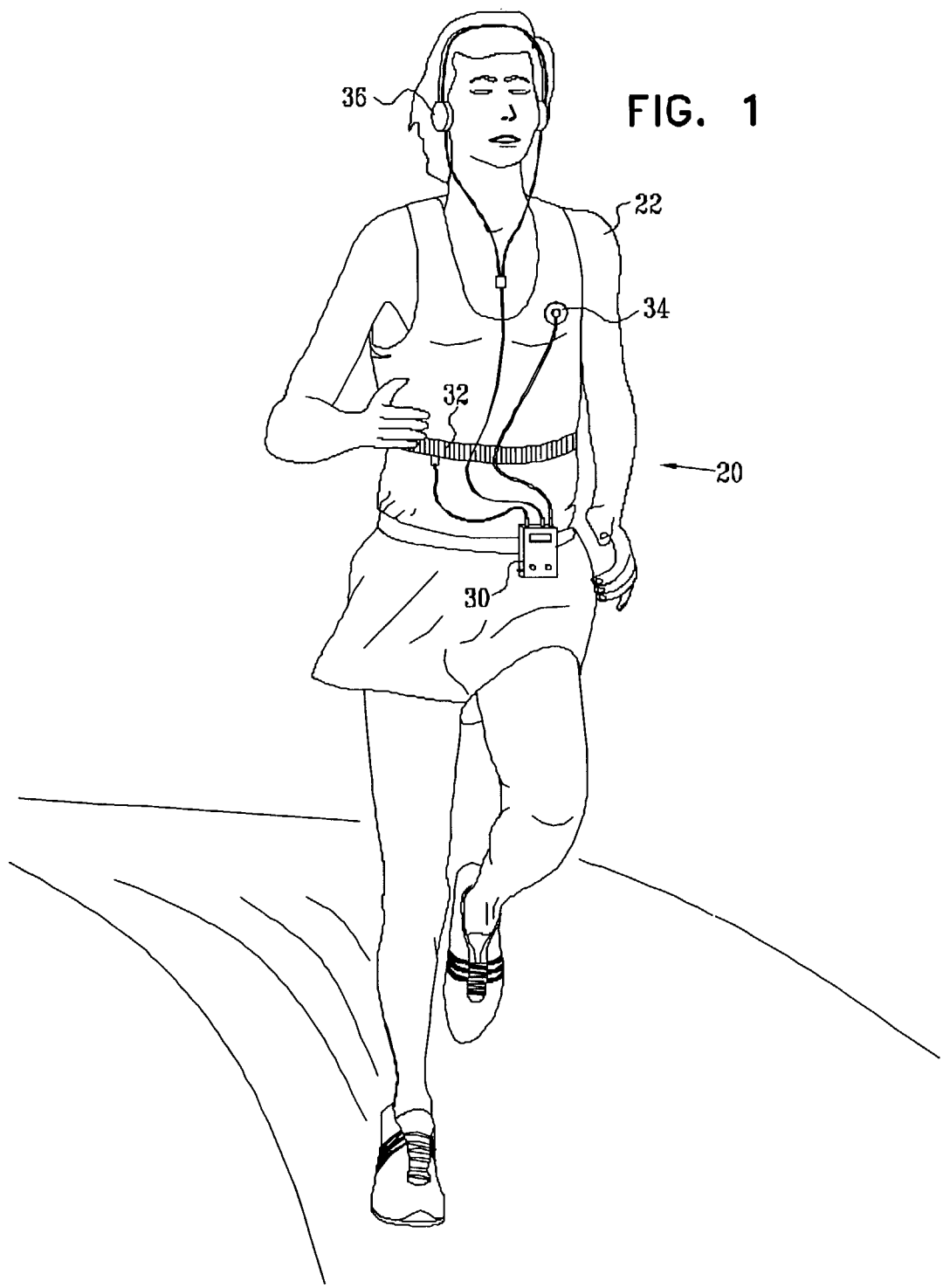
FIG. 1 is a schematic pictorial illustration of a system for beneficial modification of biorhythmic activity of a user, in accordance with an embodiment of the present invention.

FIG. 1 is a schematic pictorial illustration of a system 20 for beneficial modification of biorhythmic activity of a user 22, in accordance with an embodiment of the present invention. System 20 comprises a control unit 30, which receives biorhythmic-activity signals from at least one physiological sensor 32 coupled to the user. The control unit may also receive health status signals from one or more health status sensors 34, and/or from sensor 32. Control unit 30, the sensors, the sensor signals, and the health status signals are described in greater detail hereinbelow. The connection between control unit 30 and sensors 32 and 34 may be wired or wireless.

Control unit 30 analyzes the received sensor signals, and, responsive to the analysis, performs an intervention on user 22, typically by generating a user output signal using a stimulation unit 36, which may, for example, comprise headphones or other speakers, for applications in which the output signal is audio. The output signal directs the user to modify a parameter of a voluntary action, so as to cause an improvement in a physiological variable of the user. During a typical session of use, the device continuously senses biorhythmic activity and modifies the intervention responsive to the analysis of the activity. The user typically uses the device during multiple sessions that extend over a period of time, generally days, months or years. Each session typically has a length of between about 10 and about 20 minutes, most typically about 15 minutes.

For some applications, sensor 32 comprises a force transducer for monitoring breathing movements, including the timing and the depth of the inspiratory and expiratory phases of the user's respiration, typically via changes in chest or abdominal circumference, based on a strain-gauge which is attached to an elastic belt, such as those described in the above-referenced U.S. Pat. No. 5,423,328 and U.S. patent application Ser. No. 09/611,304 and '049 PCT Publication. Typically, sensor 32 is self-installed by user 22.

Figure 2:
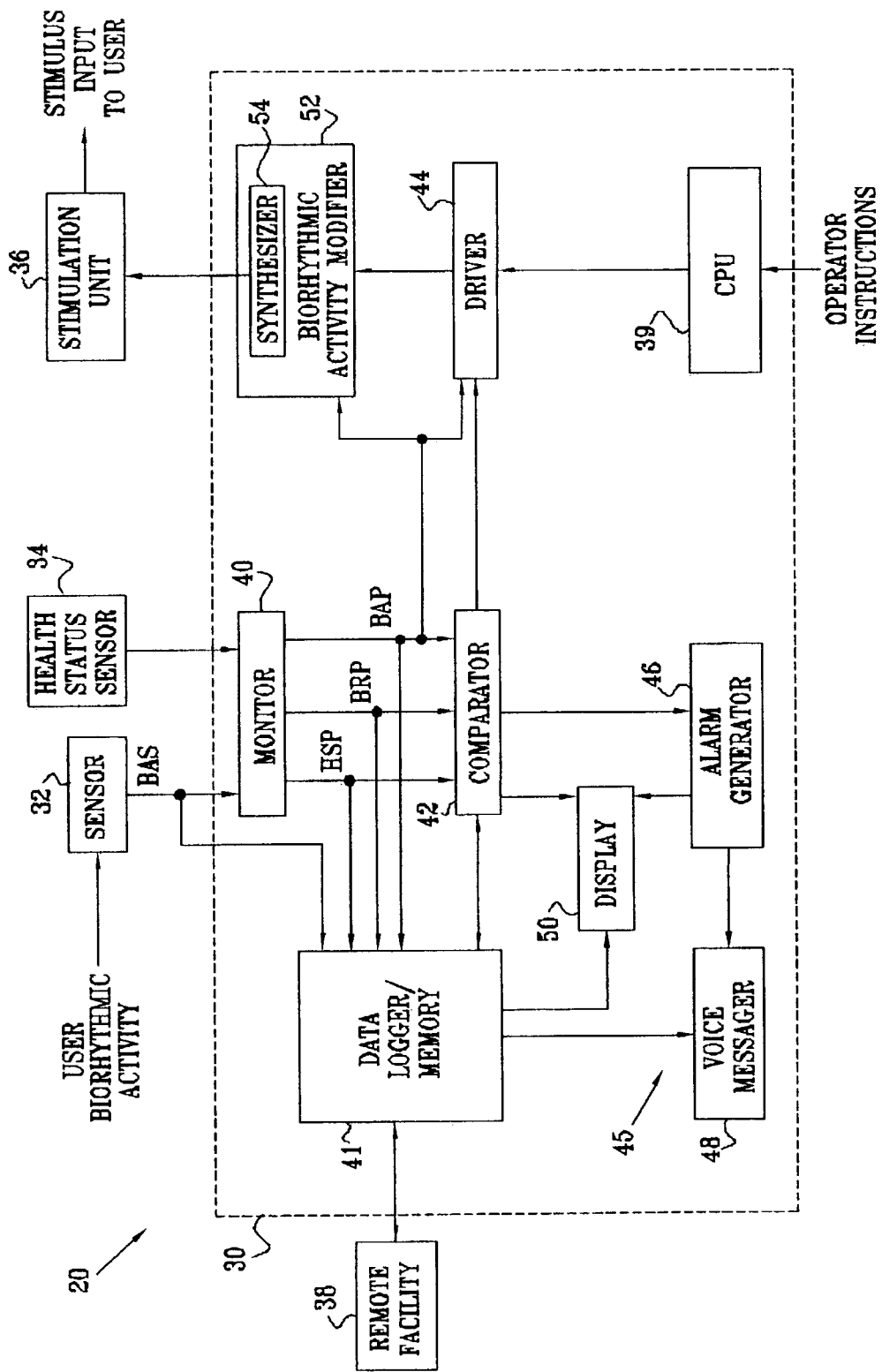
FIG. 2 is a schematic block diagram showing components of a control unit of the system of FIG. 1, in accordance with an embodiment of the present invention.

FIG. 2 is a schematic block diagram showing components of control unit 30, in accordance with an embodiment of the present invention. Control unit 30 is implemented in discrete components or a combination of discrete and custom or semi-custom components. Alternatively, control unit 30 comprises an industry-standard or customized computer coupled to a display, which is programmed in software to carry out the functions described herein. This software may be downloaded to the control unit in electronic form, over a network, for example, or it may alternatively be provided on tangible media, such as magnetic or optical media or other non-volatile memory.

Control unit 30 comprises a central processing unit (CPU) 39, which is coupled to and controls the operation of the individual components of the control unit. For clarity, lines are not shown between CPU 39 and the other components. CPU 39 can be operated in one or more different modes pursuant to operator instructions, as described hereinbelow.

A monitor 40 receives a biorhythmic-activity signal (BAS) from sensor 32, and typically identifies a first and second characteristic thereof. The first characteristic is indicative of a voluntary action of the user (e.g., the timing of inspiration and expiration), and is typically one aspect of the user's biorhythmic activity. The second characteristic is indicative of a physiological variable of the user that is desired to be improved and over which most persons do not usually exert voluntary control (a "benefit-related variable"), e.g., depth or regularity of inspiration. Monitor 40 typically also identifies a third characteristic of the BAS, which is indicative of a general physiological state of the user (a "health status variable"). Alternatively or additionally, monitor 40 receives indications of one or more health status variables from optional health status sensor 34, or from an optional keyboard coupled to or integrated with system 20, or by connecting the system to a computer. Monitor 40 analyzes these characteristics, and responsive to the analysis outputs the following quantitative parameters, which represent one or more pattern components of the sensed biorhythmic activity of the user:

- one or more biorhythmic activity parameters (BAP), derived from the first characteristic of the BAS, and used to define in general the stimulus pattern used for the intervention (for example, (a) inspiration time and expiration time, and/or (b) amplitude, when sensor 32 monitors breathing movements). Techniques described herein may be implemented using details of the BAP described in the above-referenced U.S. Pat. Nos. 5,076,281 and 5,800,337;
- one or more benefit-related parameters (BRP) derived from the second characteristic, and associated with one or more benefit-related variables of the user, for example, breathing pattern regularity. Typically, benefit-related variables include parameters of the user that are altered by a pathology or other phenomenon of user 22 that is being treated by system 20. For example, benefit-related variables may include continuously-measured or intermittently-measured blood pressure, blood oxygenation (e.g., SpO2), pulse-wave velocity, variations in skin blood volume, respiration parameters (e.g., peak air flow), or an electrocardiogram (ECG) measurement of user 22. For some applications, the BRP are derived from detected relationships between two or more first characteristics; and
- one or more health status parameters (HSP), derived from the third characteristic and/or from the signal received from health status sensor 34, the keyboard, or the external computer, and associated with physiological variables which it is desired to keep in prescribed limits to avoid undesired effects. Examples of HSP include respiration rate, which may be monitored to avoid hyperventilation; heart rate, which may be monitored to prevent the use of system 20 when even a minimal effort may cause tachycardia in patients with severe heart failure; ECG; blood pressure; and/or non-biorhythmic indicators such as weight, height, and age. As appropriate, control unit 30 evaluates the HSP to determine whether they are within safe ranges. For example, for a user having a specified gender, age, and weight, a certain measured heart rate may be determined to be too high or too low, and thus force a premature termination of the intervention and an alarm signal.

These parameters are typically stored, continuously or intermittently, in a data logger/memory 41, which typically comprises industry-standard volatile and non-volatile memory components. Additionally, in some configurations of system 20, or in an operator-selected mode, the BAS received from sensor 32 are stored continuously or intermittently in data logger 41. Storage of the BAS may be particularly useful when a physician desires access to the detailed structure of the biorhythmic activity, such as for diagnostic purposes. For example, abnormal breathing patterns are often complex, and physicians may be more familiar with and comfortable using the raw signal than its analyzed structure. For some applications, data logger 41 additionally stores the date and time of use of the system, received from an internal clock (not shown). The optional use of an interchangeable data logger, facilitated for example by a smart card or user ID's and passwords, enables multiple users to use the device, each retaining his or her own stored data.

For some applications, control unit 30 is configured to operate in a diagnostic mode, in which the system does not perform an intervention. In this mode, the control unit stores the stored data in data logger 41, for later analysis.

Data logger 41 typically retains stored data from multiple sessions of use of the system. Stored data may include trends calculated from previous sessions, and can be displayed alpha-numerically or graphically by the device pursuant to operator instructions. The stored data may enable evaluation of the success of a routine or repeated use of the system. Additionally, some aspects of the stored data (including current and past use of the device) can be displayed so as to provide help and feedback to the user. For example, the displayed data may motivate the user to make the desired modifications to biorhythmic activity, during an intervention or when the user is not currently using the system.

A comparator 42 receives values of BAP, BRP, and HSP, and compares these values with values that have been previously stored in data logger 41, in order to evaluate changes over time of these parameters. Such comparisons are useful for evaluating the sustained benefit of routine use of system 20. Such comparisons are also useful for identifying deviations in measured values of physiological variables from benchmark values for such physiological variables. Such benchmark values include, but are not limited to: (a) normative values, based on predetermined or operator-pre-selected values; (b) the most probable values characteristic of the user, as determined by comparator 42 using statistical methods applied to the data stored in data logger 41; and (c) values characterizing the recommended usage of the system, as preset by the manufacturer or pre-selected by the operator.

Comparator 42 typically derives a further set of parameters, herein termed cross-correlation parameters (CCP), from values of BAS, BAP, BRP and HSP stored in data logger 41 for a predetermined duration. CCP are typically derived by temporal correlation or by spectral cross-correlation analysis, which are mathematical techniques known in the art. Typical CCP data characterize cardiovascular reflexes as a degree of respiratory modulation of heart rate. Typically, CCP data are stored in data logger/memory 41, and are passed by comparator 42 to a driver 44, described hereinbelow.

For some applications, comparator 42 operates using techniques described in the above-referenced U.S. patent application Ser. No. 09/611,304 and '049 PCT Publication, including, but not limited to, the methods shown in and described with reference to FIG. 4 thereof.

When it is desired, typically in accordance with predetermined criteria, to notify the user of the occurrence of unexpected values in its inputs, comparator 42 provides feedback to the user using an audiovisual messaging system 45. The messaging system comprises an alarm generator 46, and a voice messager 48 and/or a display 50, which may be activated by the alarm generator. Typical messages generated by the messaging system include:

- error messages, which indicate incorrect use of the system, such as inappropriate mounting of sensors 32 or 34 (which may result in a meaningless or no BAS signal), or not following the system usage guidelines (which may diminish the effectiveness of the system). The message typically includes suggested corrective action;
- exercise guidance messages, which are typically verbal and/or visual instructions that may help guide an inexperienced user in modifying his or her biorhythmic activity after receiving the user stimulus;
- warning messages, which instruct the user regarding which actions to take if undesired values of physiological parameters occur, e.g., to stop the exercise if the heart rate becomes too fast; and
- summary messages, which provide the user with a summary of his or her compliance with the intervention, and/or with performance data.

Alternatively or additionally, CPU 39 modifies the setup of the system in accordance with the type of unexpected value indicated by comparator 42. For example, CPU 39 may change the user stimulus from: (a) a guiding type of stimulus, intended to guide the user through changes in a behavior (e.g., decreases in Inspiration: Expiration ratio), to (b) a neutral type of stimulus, intended to maintain the I:E ratio while heart rate or blood pressure achieve or return to desired values, or to (c) a null type of stimulus, such as the sound of ocean waves, having no guiding or maintaining component whatsoever, but designed to keep the patient's focus.

The user and/or the operator are typically able to set preferences regarding the operation of messaging system 45. For example, voice messager 48 may be configurable to be activated:

- at all times, i.e., to provide a human voice that helps the user to synchronize biorhythmic activity with the user stimulus;
- only when user does not synchronize his or her biorhythmic activity with the user stimulus; or
- only when the voice message is essential for proper operation, e.g., when no biorhythmic activity signal is detected for a predetermined period of time, or when the battery is discharged, which causes the CPU to shut off the control unit.

Providing such preferences is advantageous for some therapeutic applications that include routine use of the device, as an inexperienced user may prefer the first option, while a more experienced user may prefer the third option. Typically, the use of voice and visual messages is minimized, so as to avoid distracting the user.

In an embodiment of the present invention, data logger 41 or CPU 39 activates display 50 or voice messager 48 to present the user with a questionnaire, to which the user typically responds by pressing buttons. The responses are stored and may be useful, for example, in evaluating clinical outcomes, such as quality of life.

A biorhythmic activity modifier 52 provides user 22 with a user stimulus, configured to change at least one aspect of the user's biorhythmic activity. The user stimulus is transmitted to user 22 using stimulation unit 36. Biorhythmic activity modifier 52 obtains the parameters used for generating the user stimulus by transforming the BAP values by applying a set of rules received from driver 44. For example, the user stimulus may be a sound pattern, which varies over time to teach user 22 to alter a time period associated with inspiration and/or expiration.

In an embodiment, biorhythmic activity modifier 52 comprises a sound synthesizer 54. (In other embodiments, modifier 52 comprises, for example, a mechanical stimulator, an electrical stimulator, a pressure applicator, or a visual stimulator.) The synthesizer generates an audio output, typically in which the sound of a first instrument, such as a flute, corresponds to inspiration, and the sound of a second instrument, such as a guitar, corresponds to expiration. The operation of synthesizer 54 is typically controlled by stored sequences of codes that define the musical notes and the instruments with ON/OFF commands, in order to create a user-selectable melody. For example, the duration of the sound of the first instrument may be 2% larger than the user's average inspiration time during the last minute, and the duration of the sound of the second instrument may be 10% larger than the average expiration time during the last 5 minutes, where the transformation parameters (e.g., 2%, 1 minute, 10%, 5 minutes) are received from driver 44. Biorhythmic activity modifier 52 and driver 44 may implement techniques described in the above-referenced U.S. Pat. Nos. 5,076,281 and 5,800,337 and U.S. patent application Ser. No. 09/611,304 and '049 PCT Publication.

For some applications, control unit 30 is connected to a remote facility 38, such as a hospital or medical clinic, for uploading and downloading of data for remote viewing and/or analysis, in real time or intermittently. Typically, remote facility 38 communicates with control unit 30 and/or user 22 via a distributed network such as the Internet. Alternatively or additionally, the remote facility communicates with the control unit and/or the user by other means known in the art, for example by a telephone modem or by voice, using a telephone. The remotely-mediated techniques described in the above-referenced U.S. patent application Ser. No. 09/611,304 and '049 PCT Publication may be used for such remote communication and analysis.

In an embodiment of the present invention, all or a portion of the content of data logger 41 is downloaded, modified and/or erased by commands received from remote facility 38, or locally by using operator commands optionally known to an operator but not the user, e.g., pressing on a combination of buttons. For some applications, some aspects of the stored data are displayable offline in order to provide the user with information about prior usage of the device. Alternatively or additionally, such offline display enables an operator, such as a healthcare provider, to remotely provide technical support to the user (typically during a telephone conversation). For example, the operator may request that the user read from the display the content of relevant memory locations that provide data useful for resolving operational problems.

Figure 3:
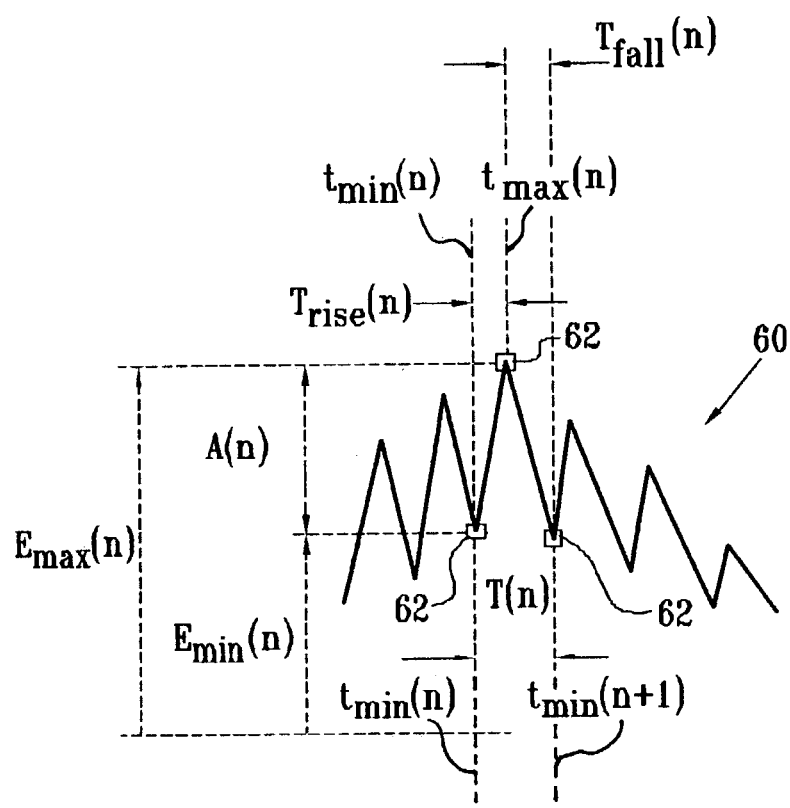
FIG. 3 is a schematic illustration of a typical monitored biorhythmic activity signal, in accordance with an embodiment of the present invention.

FIG. 3 is a schematic illustration of a typical monitored BAS 60, including exemplary special points 62 characterizing the signal's structures, in accordance with an embodiment of the present invention. The special points may be used in the determination of the parameters BAP, BRP and HSP by monitor 40. This determination is typically made by performing specific time-point analyses of the respective signals. For example, such analyses may include: (a) taking the time derivative of the signal at one or more special points, (b) determining a maximum or minimum of the time derivative, and/or (c) determining a difference in time or in signal value between two of the special points that characterize a biorhythmic cycle. The analysis may also include averaging activity occurring over two or more biorhythmic cycles. The special points may be, for example, maxima, minima, and turning points (e.g., as described in the above-referenced U.S. Pat. No. 5,800,337). The detection of these and other special points may be performed using techniques described in the above-referenced U.S. Pat. No. 5,800,337.

The example shown in FIG. 3 is for illustrative purposes only. The example assumes that an $n^{th}$ cycle of biorhythmic activity of a user can be characterized by one minimum point at $[t_{min}(n), E_{min}(n)]$, and one maximum point at $[t_{max}(n), E_{max}(n)]$, where $t_{min}(n)$ and $t_{max}(n)$ represent time values, and $E_{min}(n)$ and $E_{max}(n)$ represent signal values. Thus, $E_{max}(n)$ represents the upper envelope of the biorhythmic activity at the $n^{th}$ cycle, and $E_{min}(n)$ represents the lower envelope of the biorhythmic activity at the $n^{th}$ cycle. Both envelopes are optionally converted over time into smooth curves, typically using standard methods such as cubic spline approximation. The amplitude of the biorhythmic activity is defined by the equation $A(n)=E_{max}(n)-E_{min}(n)$ (after smoothing, if smoothing was performed). The period T(n) of the biorhythmic activity is defined as $T(n)=t_{min}(n+1)-t_{min}(n)$. The rise time $T_{rise}(n)$ and the fall time $T_{fall}(n)$ of the biorhythmic activity are defined as $T_{rise}(n)=t_{max}(n)-t_{min}(n)$ and $T_{fall}(n)=t_{min}(n+1)-t_{max}(n)$, respectively.

The detection of these and other special points can be readily generalized to cycles of multi-phase biorhythmic activity given by $[t(n,j), E(n,j)]$, marking the $j^{th}$ special point in the $n^{th}$ cycle. In this case, E(n,k) spans the envelopes, the amplitudes $A(n,j,k)=E(n,k)-E(n,j)$, and the corresponding time segments $T(n,j,k)=t(n,k)-t(n,j)$.

Figure 4:
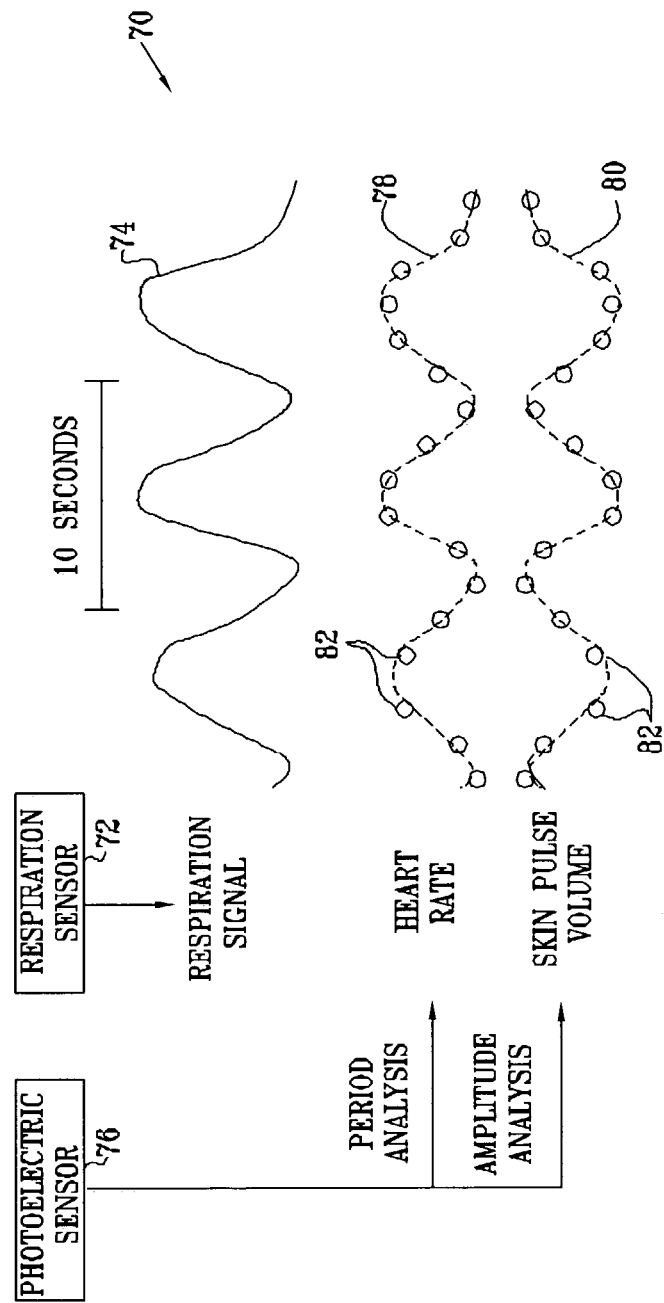
FIG. 4 is a schematic illustration of several monitored biorhythmic activity signals, in accordance with an embodiment of the present invention.

FIG. 4 is a schematic illustration of several monitored BAS 70, in accordance with an embodiment of the present invention. In this embodiment, system 20 comprises a plurality of physiological sensors 32 adapted to measure cardiovascular reflexes. The sensors generate a plurality of sensor BAS 70. Typically one of the sensors comprises a respiration sensor 72, which provides a continuous respiration signal 74. Another one of the sensors comprises a photoelectric sensor 76, which performs photoplethysmography in order to monitor (typically in AC mode) pulsatile skin blood volume changes, and to provide a heart rate signal 78 and a skin pulse volume signal 80, after using a beat-to-beat analysis of period and amplitude (values marked by circles 82), respectively. This embodiment is typically used in interventions designed to slow breathing, increasing baroreflex sensitivity.

Figure 5:
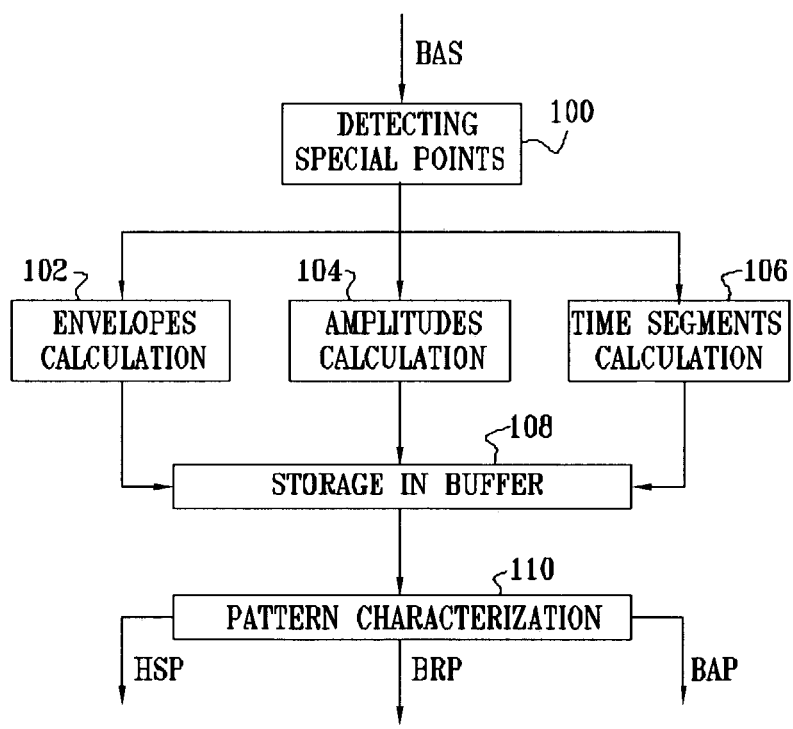
FIG. 5 is a flow chart illustrating a method for operating a monitor of the device of FIG. 1, in accordance with an embodiment of the present invention.

FIG. 5 is a flow chart illustrating a method for operating monitor 40, in accordance with an embodiment of the present invention. At a special point detection step 100, special points are detected using BAS, typically as described hereinabove with reference to FIG. 3. A beat-to-beat analysis is performed by calculating envelopes, amplitudes, and time segments, at respective calculation steps 102, 104, and 106. The results of the beat-to-beat analysis are stored for further analysis in a buffer, which may be a component of data logger 41, at a buffer storage step 108. Biorhythmic activity pattern characterization is performed to generate the parameters BAP, BRP, and HSP, at a pattern characterization step 110. The process of generating the pattern characterizations is typically specific to the nature of the biorhythmic activity and its modification by the disease pathology or by the user's condition. (For example, breathing at high altitudes becomes abnormal and similar to that of CHF patients.) The calculation of BAP may be performed using techniques described in the above-referenced U.S. Pat. Nos. 5,076,281 and 5,800,337.

In an embodiment of the present invention, the voluntary action of the user comprises respiration, and the modifiable parameters of the voluntary action include one or more timing parameters of the respiration. The user stimulus typically comprises an intelligible stimulus, such as a sound pattern and/or dynamic graphical pattern, which is generated by the device responsive to the analysis according to one or more predefined criteria. The stimulus is typically intended to modify respiration of the user, for example, by training the user to initiate a new breathing pattern. For example, the output signal may direct the user to change the timing of inspiration and expiration so as to cause a reduction in a ratio of inspiration to expiration (the I:E ratio). For some interventions, it is desirable to reduce this ratio, for example, typically, to 1:4, from a pre-intervention level typically of 1:1 or 1:2. For some applications, the benefit-related variable is an amplitude of the respiration, and changes in the I:E ratio are engendered so as to cause gradual changes (e.g., during one session or over multiple sessions) in the amplitude.

In an embodiment of the present invention, BRP are associated with variability or regularity of some aspects of the sensor signal, such as envelope, amplitude or times between designated points (i.e., a period of the sensor signal). For example, such variability may be expressed as the standard deviation (SD) of an aspect, calculated for data stored during a most recent period of time, typically about one minute. An unmodified SD may be used when the sensor signal is measuring an absolutely determined biorhythmic variable, such as heart period or rate. When the variable being measured has absolute meaning but is not calibrated, e.g., skin pulse volume, a relative variability may be defined by the value of the SD divided by the mean value of the aspect over the period used to calculated the SD, for example, the SD of amplitude divided by the mean of amplitude. When the variable being measured is not calibrated and is measured against an arbitrary reference value, e.g. respiration envelopes in some sensors, the variability may be defined by the SD of the aspect divided by the mean of another related aspect, e.g., the SD of an envelope divided by the mean of a related amplitude. In an embodiment, variability of biorhythmic activity is expressed by the following equation:

$$\text{variability}=1-[\text{SD(upper envelope)}+\text{SD(amplitude)}]/\text{mean(amplitude)}$$

which approach to unity when the biorhythmic activity cycles possess almost identical structure. The inventor believes that such measures for variability or regularity as benefit-related parameters provide valuable feedback about the condition of the user and/or the efficacy of the intervention.

It is believed that respiratory modulation of heart rate (or period) and skin pulse volume reflect the functionality of the nervous system. More precisely, these physiological variables express the dynamic balance between sympathetic and parasympathetic neural activity, which is impaired in some cardiovascular diseases, such as hypertension and CHF. In an embodiment of the present invention, BRP is calculated based on this physiological understanding. In order to quantitatively isolate the respiratory contribution to the variability of respiratory modulation of heart rate (or period) and skin pulse volume, a cross-correlation analysis between (a) the respiration signal and (b) the heart rate signal or the skin pulse volume signal, is typically performed (these signals are illustrated in FIG. 4).

In an embodiment of the present invention, the HSP correspond to the mean values or trends that are desired to be maintained within limits, as described in the above-cited U.S. patent application Ser. No. 09/611,304 and '049 PCT Publication. In an embodiment, the trend of a calculated variability of one or more physiological variables is used as an HSP. For example, when respiration is used as the biorhythmic activity, and the intervention is directed towards reducing the rate of respiration as much as possible, as described in the above-mentioned U.S. Pat. No. 5,076,281, breathing regularity (an HSP) may begin to decline if the user forces himself or herself to breathe more slowly and deeply, which tends to make the intervention inefficient. Comparator 42 typically indicates the detection of such a trend to driver 44, which is programmed to guide the user to a breathing pattern with improved breathing regularity.

In an embodiment of the present invention, sensor 32 comprises a first and a second sensor, which generate a first sensor signal and a second sensor signal, respectively. The first characteristic is derived from the first and/or the second sensor signal, while the second characteristic is derived from both the first and the second sensor signals. For example, for some applications, the first and second sensors comprise respective respiration sensors that monitor abdominal breathing and thoracic breathing, respectively. In these applications, the voluntary action of the user comprises respiration, and the modifiable parameters of the voluntary action typically include one or more timing parameters of the respiration. The benefit-related variable is (a) a phase difference between abdominal breathing and thoracic breathing, which the intervention attempts to reduce; (b) a ratio of abdominal breathing amplitude to thoracic breathing amplitude, which the intervention attempts to increase; or (c) a combination of (a) and (b). For example, in CHF and COPD the abdominal muscles often exhibit reduced functionality, as indicated by a reduced ratio of abdominal to thoracic breathing amplitude. The intervention attempts to increase this ratio and thereby have a positive effect on aspects of these conditions.

In an embodiment of the present invention, sensor 32 comprises an electrocardiogram (ECG) sensor, which typically detects respiration using the impedance method. BAP is determined using the ECG sensor, and is used for guiding the respiration of the user, typically using techniques described in the above-referenced U.S. Pat. No. 5,076,281. Typically, heart rate and heart rate variability provide the HSP and BRP.

In an embodiment of the present invention, sensor 32 comprises a photoplethysmography sensor, which monitors skin blood volume changes. The signal generated by the photoplethysmography sensor contains both respiratory components and vasomotor activity components, typically at 4-8 cycles per minute, at which slow breathing guided by system 20 has a resonance-like effect with the cardiovascular system, and is associated with a reduction in peripheral vascular resistance. BRP is typically represented by the amplitude of skin pulse volume, and BAP is represented by the average frequency of skin pulse volume. Since vasoconstriction of small blood vessels, as indicated by a reduction in skin pulse volume, is an undesired effect, this parameter may additionally represent HSP for some applications.

In an embodiment of the present invention, sensor 32 comprises a set of two photoplethysmography sensors operated at different wavelengths, which together function as a pulse oximeter, which monitors blood oxygen saturation (SpO2). SpO2 is a valuable clinical indication in CHEF and COPD, as low SpO2 is associated with low oxygen supply to tissue. As such, SpO2 may be used for both BRP and HSP. Furthermore, irregular SpO2 indicates a pathological status. One or both of the sensors of the pulse oximeter also are able to generate all of the physiological variables mentioned hereinabove, for use with embodiments employing a single sensor.

In an embodiment, sensor 32 comprises a flow meter, a heated wire (for monitoring respiratory air flow), a fast-responding temperature sensor for monitoring rhythmic aspects of biorhythmic activity, a cardiac activity sensor, a muscle activity sensor, one or more electromyography (EMG) electrodes, an electroencephalogram (EEG) monitor, a microvascular property sensor, a laser Doppler sensor, a finger plethysmograph, a pressure cuff, or a strain gauge. Alternatively or additionally, sensor 32 is adapted to sense organ temperature, blood gas concentration, concentration of gases emitted from a tissue, electrical impedance of at least one organ of the user, or a change in a circumference, a volume, or a pressure of an organ of the user.

In an embodiment of the present invention, sensor 32 comprises a capnometer, which measures CO2 changes during the respiration cycle. The capnometer can function as a respiration monitor. End-tidal CO2 is an indicator of inappropriate ventilation and muscle fatigue, which generally characterize CHF and COPD pathology. End-tidal CO2 therefore may represent BAP, BRP, and/or HSP. End-tidal CO2 is of particular clinical significance during the process of weaning a patient from ventilation. In an embodiment, system 20 is used during this weaning process, optionally in conjunction with techniques described in the above-referenced U.S. patent application Ser. No. 09/611,304 and '049 PCT Publication.

In accordance with an embodiment of the present invention, sensor 32 comprises a microphone, adapted to monitor respiratory sounds, from which BAP is derived. These sounds are typically analyzed to determine an indication of the status of the user's airways, which generate the sounds with the air that flows therethrough. In asthma and other breathing-related conditions, the intervention performed by system 20 is believed to lead to relief of symptoms, as expressed in the spectrum of the respiratory sounds. Thus, the same sound may be analyzed to determine both BRP and HSP.

In an embodiment of the present invention, system 20 comprises a docking station (not shown), to which system 20 may be docked. The docking station has compartments for storing control unit 30, sensors 32 and 34, and stimulation unit 36. Typically, the control station additionally comprises a battery charger, for charging batteries of control unit 30, and a communications unit, which comprises a communications port, typically adapted to connect to an ordinary telephone jack, and means for electrically coupling the communications unit to the control unit.

In some embodiments of the present invention, the first and second characteristics (e.g., I:E ratio and inspiration amplitude) are monitored simultaneously. In other embodiments, the first and second characteristics are monitored non-simultaneously. For example, during a first phase of operation, system 20 may record a baseline measurement of values of the second characteristic, which measurement is a diagnostic indication of the physiological status of the user before undergoing the device-generated intervention. During a second phase of operation, system 20 performs the intervention responsive to this baseline measurement.

In an embodiment of the present invention, the user stimulus is in the form of a game, and the parameters of the game are altered so that playing the game induces the user to modify a parameter of the voluntary action.

In an embodiment of the present invention, control unit 30 is adapted to perform the intervention by generating a user stimulus to which the user reacts involuntarily. Typically, such an involuntary user stimulus is applied slightly out of phase with the biorhythmic activity it is desired to modify, for example, respiration. This approach may be used, for example, when the user is a subject whose autonomic control of breathing is impaired, such as an unconscious subject, for example, when the subject is in a coma or under anesthesia. Additionally, this approach may be used when the subject is sleeping, such as when the subject suffers from sleep apnea caused by the subject's inadequate control over breathing. For example, by auditory or other stimulation, the intervention may stimulate respiratory muscles of an unconscious subject who is spontaneously breathing.

Even when an intervention is applied to a conscious user, for some applications, the user semi-consciously or unconsciously modifies an aspect of voluntary action. For example, as described hereinabove, many people unconsciously and effortlessly entrain their breathing, walking, or running to an outside rhythmic stimulus, such as strongly-rhythmic music or even a blinking light. Similarly, some of these embodiments of the present invention may be applied to people who are not consciously attempting to coordinate the voluntary action with the rhythm of the applied intervention. Thus, for some applications, a user of some of these embodiments may read, talk, eat, or even sleep, while one or more sensors are measuring respective physiological variables of the user, and an intervention such as is described herein is applied to the user.

In an embodiment of the present invention, system 20 guides user 22 to change his or her breathing pattern in a way that typically increases tissue oxygenation. This application of the present invention is particularly useful in the treatment of congestive heart failure (CHF), which often causes afflicted patients to demonstrate Cheyne-Stokes respiration. This breathing pattern leads to a drop in average tissue oxygenation, because excessively-slow breathing does not supply sufficient levels of oxygen to the body, and hyperventilation places a severe load on the patient's already weak heart and does not optimally oxygenate the body. Preferably, musical patterns include musical or vocal guidance to the user to inhale and to exhale according to a schedule which gradually brings his respiration into a desired, healthy pattern, so as to increase tissue oxygenation. In accordance with a preferred embodiment of the present invention, protocols described in the above-cited articles by Mortara and Bernardi are utilized in applying the techniques described herein, so as to obtain desired increases in tissue oxygenation. The musical or vocal guidance to inhale may include, for example, a flute playing a sequence of notes which generally rises in pitch and/or volume, while the direction to exhale may include cello or guitar notes which fall in pitch and/or volume. Alternatively, the user is instructed at the beginning of the session to inhale whenever he hears a flute or a tone having a specified high pitch, and to exhale whenever he hears the cello, guitar or a tone having a specified low pitch. Preferred protocols for generating the music are described in the above-referenced U.S. patent application Ser. No. 09/611,304 and '049 PCT Publication, particularly with reference to FIG. 16 thereof.

In some applications, sensor 32 conveys signals which are indicative of skin blood volume and/or blood oxygen levels. In response, biorhythmic activity modifier 52 adjusts rhythmic parameters of the music, so as to direct the user to modify the duration of the inspiratory phase and/or the expiratory phase, and to thereby drive the signals from sensor 32 towards desired values. For example, the inventor has found that programming control unit 30 to gradually increase the proportion of respiration spent in the expiratory phase, while simultaneously gradually reducing the respiration rate to about six breaths per minute, yields the desired results of significant increases in blood oxygenation and significant decreases in blood pressure in some patients.

In a manner analogous to that described hereinabove with respect to blood oxygenation, other autonomic nervous system functions can be monitored and varied using system 20, in accordance with an embodiment of the present invention. For example, decreased heart rate variability is known in the art to be associated with cardiovascular impairment. (See, for example, the above-cited article by La Rovere et al.) To treat this phenomenon, in one application sensor 32 sends signals to control unit 30 indicative of the heart rate of user 22, and biorhythmic activity modifier 52 modifies aspects of the music or other intervention so as to increase heart rate variability. It has been shown that slow breathing increases heart rate variability. (See, for example, the above-cited article by Pitzalis et al.)

Alternatively or additionally, system 20 is operated so as to increase the mechanical compliance of the user's blood vessels. This compliance reflects the ability of blood vessels to expand in response to passage therethrough of blood ejected from the heart. Sufficient levels of arterial compliance are known to be important in buffering the pulsatile pattern of the blood pushed at high pressure from the heart, thereby smoothing the flow of blood into the microvasculature. Reduced arterial compliance, by contrast, is associated with improper function of baroreceptors which are used by the body in the feedback systems which control blood pressure. Arterial compliance is known to decrease with increasing age, as well as in many cardiovascular diseases, such as hypertension, congestive heart failure, and atherosclerosis. Moreover, arterial compliance decreases in response to an acute increase in blood pressure, and in response to increased sympathetic nervous activity, e.g., when a person is experiencing mental stress.

Preferably, system 20 increases arterial compliance in a manner generally analogous to that described hereinabove with respect to increasing blood oxygenation. Thus, biorhythmic activity modifier 52 may modify parameters of the music or other intervention presented to the user in order to determine suitable operating parameters which cause signals from sensor 32 to indicate that arterial compliance is increasing. The inventor has found that many cardiovascular indicators are optimized by causing the respiration rate or another voluntary or involuntary physiological parameter of the user to cycle at approximately 6 repetitions per minute.

Changes in arterial compliance are preferably measured by monitoring changes in the pulse wave velocity corresponding to each beat of the user's heart. Decreases in pulse wave velocity are generally desired, as they are derived from increases in arterial compliance. Changes in the pulse wave velocity are typically measured by calculating the time delay between events corresponding to the same heart beat that are measured at different distances from the heart. For example, sensor 32 may comprise electrocardiogram electrodes and a photoplethysmography sensor, and control unit 30 may measure changes in the time difference between the QRS complex of the electrocardiographic signal measured by the electrodes and the onset of a corresponding change in the photoplethysmography signal measured by the photoplethysmography sensor.

Preferably, biorhythmic activity modifier 52 sets the musical breathing directions or other applied interventions so as to maximally decrease the pulse wave velocity measurements, while substantially continuously monitoring the user's ability to comfortably adhere to the breathing or other regimen. For example, even if it were determined that an additional marginal decrease in pulse wave velocity could be attained by reducing the respiration rate from six to five breaths per minute, such a reduction would typically not be done if it were also determined that the user would take excessively large breaths at the slower rate and/or overload the heart and respiratory muscles.

For some applications of the present invention, it is desirable to apply an intervention to user 22 at a frequency between about 0.05 Hz and 0.15 Hz, which corresponds to the vasomotor frequency associated with "Mayer waves"—periodic fluctuations in lumen of the smaller blood vessels. For example, the user may be directed to breathe at the vasomotor frequency. Alternatively or additionally, stimulation unit 36 applies to other areas of the user's body cyclic doses of a mechanical input, such as positive or negative air or fluid pressure. Further alternatively or additionally, electrodes, magnets, heating or cooling units, or electromagnetic radiation emitting units placed on, in, or near the user's body, apply or remove at the vasomotor frequency corresponding forms of energy to or from the designated areas of the user's body.

In a given individual, the vasomotor frequency varies over long periods of time, and, the inventor believes, even during short time periods such as a typical 15 minute session when user 22 is interacting with system 20. Preferably, sensor 32 substantially continuously conveys signals to control unit 30 which are indicative of a current value of the vasomotor frequency of user 22. It is hypothesized that by closely matching the frequency of application of an intervention to the current value of the vasomotor frequency, system 20 is able to achieve a form of cardiovascular resonance, which induces significant improvements in known indicators of cardiovascular health. (See, for example, the above-cited article by Cook et al.) The intervention may include any of the interventions described herein, such as induced changes in respiration rate, cyclically applied mechanical pressure, heat, cooling, or application of electrical fields, magnetic fields, or various forms of electromagnetic radiation. In a preferred embodiment, one or more of these interventions is applied cyclically at the vasomotor frequency to injured tissue, in order to enhance the healing of the tissue.

In cases where a patient has COPD, it is known in the art to instruct the patient to increase his respiratory endurance by breathing 15 breaths per minute through an inspiratory load, while spending 60% of each respiratory cycle inhaling, and 40% of the cycle exhaling. Because of the high levels of mental concentration and physical effort that such an exercise requires, and because of the relatively boring nature of the task, most patients have difficulty following such a regimen, and even dedicated patients tend to stop performing the exercise except under the direct supervision of a healthcare worker.

In some embodiments of the present invention, by contrast, the mental effort is substantially eliminated, because user 22 need only listen to the music and breathe in accordance with its rhythm and pattern. In addition, by being responsive in real-time to the user's current breathing pattern, this embodiment provides significantly more functionality than would, for example, an "inhalation indicator light," which simply has a 60% duty cycle and turns on 15 times per minute. Biorhythmic activity modifier 52, by contrast, typically gradually changes the user's breathing pattern from its initial measured state (e.g., 8 breaths per minute, 30% inhale and 70% exhale) to the desired final state. Preferably, this change is caused by guiding the user's respiration through a two-dimensional parameter space defined by {[Breathing Rate], [Inspiration: Expiration Ratio]}. Typically, the processor guides the user's respiration from a point in the space representing the initial state, along the shortest path through the space, to a point in the space representing the desired final state. It is noted that the biorhythmic activity modifier preferably tracks the user's ability to breathe at each of the points along this path, and does not direct him/her to push harder towards a later goal if s/he has not successfully attained the current respiration requirement.

It is known that the respiratory system of some patients is slow to recover following surgery, and that other patients take days or weeks to successfully wean themselves from a mechanical ventilator. Therefore, some applications of the present invention are directed towards using the apparatus and methods described herein, mutatis mutandis, to gradually retrain ventilator-dependent or post-surgery patients in proper breathing techniques. Many mechanical ventilators for use with alert patients are triggered to support the patients' breathing efforts, rather than to dictate the timing and depth of every breath. Because some embodiments of the present invention utilize the user's voluntary control over his/her own breathing, it is preferable to use such triggered ventilators when employing system 20 to wean ventilator-dependent patients.

Techniques described herein may be practiced in conjunction with techniques described in the above-referenced U.S. patent application Ser. No. 09/611,304 and '049 PCT Publication.

It will be understood that whereas embodiments of the present invention have been described generally with respect to a user having a pathology, it is within the scope of the present invention for the user to be generally healthy, and to choose to use aspects of the present invention in order to obtain psychological stress-relief and/or relaxation, or for purposes of muscle re-education, athletic training, or entertainment.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. Apparatus comprising:
 a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
 an output unit; and
 a control unit, adapted to continuously:
  receive the sensor signal, and
  responsive to the first characteristic and the second characteristic, generate an output signal which drives the output unit to direct the user to modify a parameter of the voluntary action indicated by the first characteristic,
 wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentra- tion sensor, a photoelectric sensor, a pulse oximeter, a photoplethysmographic sensor, a capnometer, and a laser Doppler sensor, wherein the biorhythmic activity includes respiration, and wherein the sensor is adapted to generate the sensor signal indicative of the respiration.

2. Apparatus according to claim 1, wherein the control unit is adapted to:
identify an aspect of the first characteristic indicative of the user having modified the parameter to a desired extent, and
responsive to identifying the aspect of the first characteristic of the sensor signal, generate a new output signal, to direct the user to further modify the parameter of the voluntary action.

3. Apparatus according to claim 1, wherein the first characteristic is selected from the list consisting of: a period of an aspect of the sensor signal, a rate of an aspect of the sensor signal, a rise time of an aspect of the sensor signal, a fall time of an aspect of the sensor signal, a time derivative at a point of an aspect of the sensor signal, a maximum of the time derivative, a minimum of the time derivative, an amplitude of a maximum of an aspect of the sensor signal averaged over two or more biorhythmic cycles of the aspect, and an amplitude of a minimum of an aspect of the sensor signal averaged over two or more cycles of the aspect, and wherein the sensor is adapted to generate the sensor signal having the first characteristic.

4. Apparatus according to claim 1, wherein the first characteristic includes a time difference between two points of an aspect of the sensor signal, the points being part of a single cycle of the biorhythmic activity.

5. Apparatus according to claim 1, wherein the first characteristic includes a signal value difference between two points of an aspect of the sensor signal, the points being part of a single cycle of the biorhythmic activity.

6. Apparatus according to claim 1, wherein the second characteristic includes a variability of an aspect of the biorhythmic activity, the aspect selected from the list consisting of: an envelope of the biorhythmic activity, an amplitude of the biorhythmic activity, a period of the biorhythmic activity, a standard deviation (SD) of the envelope, an SD of the amplitude, and an SD of the period, and wherein the control unit is adapted to generate the output signal responsive to the variability of the aspect.

7. Apparatus according to claim 1, comprising a health status sensor, adapted to generate a health status signal indicative of a health status parameter of the user, which health status parameter is indicative of a state of health of the user, and wherein the control unit is adapted to receive the health status signal, and to determine whether the health status parameter passes a threshold value.

8. Apparatus according to claim 1, wherein the control unit is adapted to generate the output signal in the form of a game, and to alter parameters of the game so as to induce the user to modify the parameter of the voluntary action.

9. Apparatus according to claim 1, wherein the control unit is adapted to configure the output signal to direct the user to modify the parameter of the voluntary action so as to cause an improvement in the benefit-related variable.

10. Apparatus according to claim 9, wherein the benefit-related variable is a measure of baroreflex sensitivity of the user, and wherein the control unit is adapted to configure the output signal to direct the user to modify the parameter of the voluntary action so as to cause the improvement in the measure of baroreflex sensitivity.

11. Apparatus according to claim 9, wherein the benefit-related variable is selected from the list consisting of: a blood pressure of the user, a blood oxygenation saturation of the user, an end-tidal $CO_2$ level of the user, a tissue oxygenation level of the user, a pulse-wave velocity of the user, variations in a skin blood volume of the user, an amplitude of a skin pulse volume of the user, an arterial compliance of the user, and a parameter of an electrocardiogram of the user, and wherein the control unit is adapted to configure the output signal to direct the user to modify the parameter of the voluntary action so as to cause the improvement in the benefit-related variable.

12. Apparatus according to claim 9, wherein the control unit is adapted to configure the output signal to direct the user to modify the parameter of the voluntary action so as to cause the improvement in the benefit-related variable, so as to treat a cardiovascular disease of the user.

13. Apparatus according to claim 9, wherein the control unit is adapted to configure the output signal to direct the user to modify the parameter of the voluntary action so as to cause the improvement in the benefit-related variable, so as to treat a pulmonary disease of the user.

14. Apparatus according to claim 9, wherein the control unit is adapted to configure the output signal to direct the user to modify the parameter of the voluntary action so as to cause the improvement in the benefit-related variable, so as to treat a condition of the user selected from the list consisting of: a neurological disease, hypertension, and hyperactivity.

15. Apparatus according to claim 1, wherein the output signal includes an intelligible stimulus, and wherein the control unit is adapted to generate the intelligible stimulus, so as to direct the user to modify the parameter of the voluntary action.

16. Apparatus according to claim 15, wherein the intelligible stimulus includes at least one stimulus selected from the list consisting of: an image, alpha-numeric text, a sound, a sound pattern, and a dynamic graphical pattern, and wherein the control unit is adapted to generate the stimulus, so as to direct the user to modify the parameter of the voluntary action.

17. Apparatus according to claim 15, wherein the control unit is configured to generate an error message indicative of incorrect use of the apparatus.

18. Apparatus according to claim 17, wherein, in generating the error message, the control unit is configured to indicate inappropriate mounting of the sensor.

19. Apparatus according to claim 17, wherein, in generating the error message, the control unit is configured to indicate non-compliance with usage guidelines of the apparatus.

20. Apparatus according to claim 17, wherein, in generating the error message, the control unit is configured to identify an act which may diminish effectiveness of the apparatus.

21. Apparatus according to claim 17, wherein, in generating the error message, the control unit is configured to suggest corrective action.

22. Apparatus according to claim 15, wherein the control unit is configured to generate an exercise guidance message.

23. Apparatus according to claim 22, wherein, in generating the exercise guidance message, the control unit is configured to generate a verbal message.

24. Apparatus according to claim 22, wherein, in generating the exercise guidance message, the control unit is configured to generate a visual message.

25. Apparatus according to claim 22, wherein, in generating the exercise guidance message, the control unit is configured to generate a message suitable for guiding an inexperienced user to modify the biorhythmic activity.

26. Apparatus according to claim 15, wherein the control unit is configured to generate a voice message.

27. Apparatus according to claim 15, wherein the control unit is configured to generate a warning message.

28. Apparatus according to claim 27, wherein the control unit is configured to generate the warning message in response to an indication of an undesired value of a physiological parameter.

29. Apparatus according to claim 27, wherein the control unit is configured to generate the warning message in response to an indication that a heart rate of the user is too fast.

30. Apparatus according to claim 15, wherein the control unit is configured to generate a summary message, indicative of compliance of the user.

31. Apparatus to claim 15, wherein the control unit is configured to generate an indication of performance data of the user.

32. Apparatus according to claim 1, wherein the sensor is adapted to generate the sensor signal having a third characteristic indicative of a health status parameter of the user, which health status parameter is indicative of a state of health of the user, and wherein the control unit is adapted to determine whether the health status parameter passes a threshold value.

33. Apparatus according to claim 32, wherein the control unit is adapted to withhold generating the output signal responsive to determining that the third characteristic passes the threshold value.

34. Apparatus according to claim 32, wherein the control unit is adapted to generate an alarm signal responsive to determining that the third characteristic passes the threshold value.

35. Apparatus according to claim 1, wherein the voluntary action includes the respiration, and wherein the control unit is adapted to generate the output signal to direct the user to modify a parameter of the respiration.

36. Apparatus according to claim 35, wherein the first characteristic includes at least one breathing parameter selected from: inspiration time and expiration time, and wherein the sensor is adapted to generate the sensor signal having the first characteristic.

37. Apparatus according to claim 35, wherein the first characteristic includes an average frequency of a skin pulse volume of the user, and wherein the sensor is adapted to generate the sensor signal having the first characteristic.

38. Apparatus according to claim 35, wherein the first characteristic includes an end-tidal CO2 level of the user, and wherein the sensor is adapted to generate the sensor signal having the first characteristic.

39. Apparatus according to claim 35, wherein the parameter of the respiration includes one or more timing parameters of the respiration, and wherein the control unit is adapted to generate the output signal to direct the user to modify the timing parameters of the respiration.

40. Apparatus according to claim 39, wherein the timing parameters include a pattern of inspiration and expiration of the user, and wherein the control unit is adapted to generate the output signal to direct the user to modify the pattern.

41. Apparatus according to claim 40, wherein the control unit is adapted to generate the output signal to direct the user to modify the pattern so as to reduce a ratio of a time period of the inspiration to a time period of the expiration.

42. Apparatus according to claim 1, wherein the sensor comprises a finger plethysmograph.

43. Apparatus according to claim 1, wherein the first characteristic includes a plurality of first characteristics indicative of the voluntary action of the user, and wherein the control unit is adapted to generate the output signal responsive to at least one relationship among the plurality of first characteristics.

44. Apparatus according to claim 1, wherein the sensor comprises the photoplethysmographic sensor.

45. Apparatus comprising:
a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
an output unit; and
a control unit, adapted to continuously:
receive the sensor signal, and
responsive to the first characteristic and the second characteristic, generate an output signal which drives the output unit to direct the user to modify a parameter of the voluntary action indicated by the first characteristic,
wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentration sensor, a photoelectric sensor, a pulse oximeter, a photoplethysmographic sensor, a capnometer, and a laser Doppler sensor,
wherein the control unit is adapted to configure the output signal to direct the user to modify the parameter of the voluntary action so as to cause an improvement in the benefit-related variable, and
wherein the benefit-related variable is an amplitude of respiration of the user, and wherein the control unit is adapted to configure the output signal to direct the user to modify the parameter of the voluntary action so as to cause the improvement in the amplitude of the respiration.

46. Apparatus comprising:
a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
an output unit;
a control unit, adapted to continuously:
receive the sensor signal, and
responsive to the first characteristic and the second characteristic, generate an output signal which drives the output unit to direct the user to modify a parameter of the voluntary action indicated by the first characteristic,
wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentration sensor, a photoelectric sensor, a pulse oximeter, a photoplethysmographic sensor, a capnometer, and a laser Doppler sensor,
wherein the output unit comprises a speaker,
wherein the output signal includes an intelligible stimulus, and wherein the control unit is adapted to generate the intelligible stimulus, so as to direct the user to modify the parameter of the voluntary action,
wherein the intelligible stimulus includes music, and wherein the control unit is adapted to drive the speaker to generate the music, so as to direct the user to modify the parameter of the voluntary action.

47. Apparatus comprising:
- a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
- an output unit; and
- a control unit, adapted to continuously:
    - receive the sensor signal, and
    - responsive to the first characteristic and the second characteristic, generate an output signal which drives the output unit to direct the user to modify a parameter of the voluntary action indicated by the first characteristic,
- wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentration sensor, a photoelectric sensor, a pulse oximeter, a photoplethysmographic sensor, a capnometer, and a laser Doppler sensor,
- wherein the first characteristic includes a plurality of first characteristics indicative of the voluntary action of the user, and wherein the control unit is adapted to generate the output signal responsive to at least one relationship among the plurality of first characteristics, and
- wherein the control unit is adapted to determine the relationship using an analysis technique selected from: cross-correlation analysis in a frequency domain and cross-correlation analysis in a time domain.

48. Apparatus comprising:
- a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
- an output unit; and
- a control unit, adapted to continuously:
    - receive the sensor signal, and
    - responsive to the first characteristic and the second characteristic, generate an output signal which drives the output unit to direct the user to modify a parameter of the voluntary action indicated by the first characteristic,
- wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentration sensor, a photoelectric sensor, a pulse oximeter, a photoplethysmographic sensor, a capnometer, and a laser Doppler sensor,
- wherein the first characteristic includes a relationship among two or more spectral components that are defined by points in the sensor signal.

49. Apparatus comprising:
- a sensor, adapted to generate a sensor signal indicative of a given biorhythmic activity of a user of the apparatus, the sensor signal having a first characteristic, indicative of a voluntary action of the user, and a second characteristic, indicative of a benefit-related variable of the user;
- an output unit; and
- a control unit, adapted to continuously:
    - receive the sensor signal, and
    - responsive to the first characteristic and the second characteristic, generate an output signal which drives the output unit to direct the user to modify a parameter of the voluntary action indicated by the first characteristic,
- wherein the sensor is selected from the group consisting of: a sensor adapted to generate a sensor signal indicative of cardiac activity, a fast-responding temperature sensor, an electrocardiogram (ECG) monitor, at least one electromyography (EMG) electrode, a blood gas concentration sensor, a photoelectric sensor, a pulse oximeter, a photoplethysmographic sensor, a capnometer, and a laser Doppler sensor,
- wherein the first characteristic includes at least one spectral component that is defined by points in the sensor signal.

50. Apparatus according to claim 49, wherein the spectral component is defined by a first subset of points in the sensor signal, the first subset of points being located among a second subset of points in the sensor signal different from the first subset of points, the first subset of points sharing a common property.

51. Apparatus according to claim 50, wherein the common property is selected from the list consisting of: local maxima and local minima of the sensor signal.

\* \* \* \* \*